United States Patent
Barber et al.

(10) Patent No.: US 9,480,802 B2
(45) Date of Patent: Nov. 1, 2016

(54) CHILD-RESISTANT CLOSURE SYSTEMS FOR CONTAINERS

(71) Applicant: TAPTANGO, LLC, Gainesville, VA (US)

(72) Inventors: Launce R. Barber, Richmond, VA (US); Thomas J. A. Zuber, Fort Lee, NJ (US); Corey R. Vaughan, Seattle, WA (US)

(73) Assignee: TAPTANGO, LLC, Gainesville, VA (US)

( * ) Notice: Subject to any disclaimer, the term of this patent is extended or adjusted under 35 U.S.C. 154(b) by 0 days.

(21) Appl. No.: 14/796,193

(22) Filed: Jul. 10, 2015

(65) Prior Publication Data
US 2015/0320943 A1    Nov. 12, 2015

Related U.S. Application Data

(63) Continuation of application No. 14/216,595, filed on Mar. 17, 2014, now abandoned.

(60) Provisional application No. 61/802,060, filed on Mar. 15, 2013.

(51) Int. Cl.
*B67B 1/00* (2006.01)
*A61M 11/00* (2006.01)
(Continued)

(52) U.S. Cl.
CPC ............ *A61M 11/00* (2013.01); *A61M 11/006* (2014.02); *A61M 15/0025* (2014.02); *A61M 15/08* (2013.01); *B05B 11/0027* (2013.01); *B05B 11/0032* (2013.01); *B05B 11/3059* (2013.01); *B65D 47/127* (2013.01); *B65D 50/04* (2013.01);
(Continued)

(58) Field of Classification Search
CPC ............ B05B 11/3059; B05B 11/306; B05B 11/0027; B05B 11/0005; B05B 11/0032; B05B 15/02; A61M 15/0025; A61M 15/08; A61M 11/00; A61M 11/006; B65D 83/40; B65D 83/205; B65D 47/127; B65D 50/04
USPC ............ 222/153.01, 153.1, 153.09–153.14, 222/321.6–321.9, 401, 402.11, 402.13, 222/402.15
See application file for complete search history.

(56) References Cited

U.S. PATENT DOCUMENTS

| | | |
|---|---|---|
| 4,244,495 A | 1/1981 | Lorscheid et al. |
| 4,801,093 A | 1/1989 | Brunet et al. |

(Continued)

OTHER PUBLICATIONS

USPTO Office Action for U.S. Appl. No. 14/216,639, dated Mar. 10, 2015, 9 pages.

*Primary Examiner* — Lien Ngo
(74) *Attorney, Agent, or Firm* — Patent Law of Virginia, PLLC; Brian J. Teague

(57) ABSTRACT

A child-resistant closure system for a pump sprayer comprises a cap, a dispensing tip configured to receive the cap thereon, and a base secured to the dispensing tip and secured to a dispenser bottle. The tip has a slot defined therein that comprises a wider insertion/removal portion for inserting or removing a downwardly extending leg and a narrower locking portion for engaging the leg to lock the cap to the dispensing tip. The cap is selectively secured to the dispensing dip by rotating the cap such that the leg moves from the wider portion of the slot to the narrower portion of the slot, such that the narrower portion of the slot engages leg. The leg extends downward through the slot to contact the top of the base so as to allow for the sprayer pump unit to be locked out from operation.

3 Claims, 30 Drawing Sheets

(51) Int. Cl.
*A61M 15/00* (2006.01)
*B05B 11/00* (2006.01)
*B65D 50/04* (2006.01)
*B65D 47/12* (2006.01)
*A61M 15/08* (2006.01)
*A61F 9/00* (2006.01)

(52) U.S. Cl.
CPC ........... *A61F 9/0008* (2013.01); *A61M 15/009* (2013.01); *A61M 2205/276* (2013.01); *B65D 2215/02* (2013.01)

(56) References Cited

U.S. PATENT DOCUMENTS

| | | | |
|---|---|---|---|
| 4,944,429 A | 7/1990 | Bishop et al. | |
| 5,492,251 A | 2/1996 | Albini et al. | |
| 6,164,498 A * | 12/2000 | Faughey | B05B 11/3008 222/153.13 |
| 6,926,174 B1 * | 8/2005 | Heldt | B05B 11/0027 215/321 |
| 7,168,594 B2 | 1/2007 | Law et al. | |
| 8,104,643 B2 * | 1/2012 | Pruvot | B05B 11/3059 222/153.06 |
| 9,352,348 B2 * | 5/2016 | Greiner-Perth | B05B 11/0032 |
| 2005/0098172 A1 * | 5/2005 | Anderson | B05B 11/3091 128/200.23 |
| 2008/0210229 A1 * | 9/2008 | Corbacho | A61M 15/0028 128/200.22 |
| 2008/0245896 A1 * | 10/2008 | Welp | B05B 11/0032 239/333 |
| 2013/0175303 A1 * | 7/2013 | Donnette | B05B 11/3004 222/321.6 |
| 2013/0270298 A1 * | 10/2013 | Dejonge | B05B 11/0032 222/162 |
| 2014/0263455 A1 * | 9/2014 | Keenan | A61M 15/0026 222/153.13 |
| 2015/0284177 A1 * | 10/2015 | Patil | B05B 11/0027 222/153.04 |

\* cited by examiner

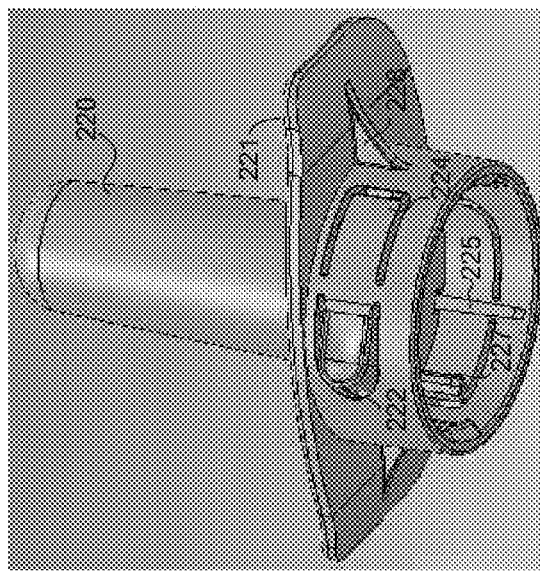
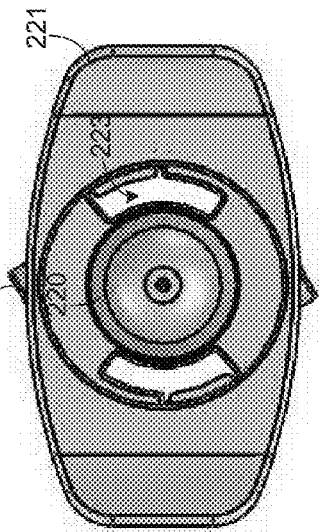
FIG. 9
FIG. 10
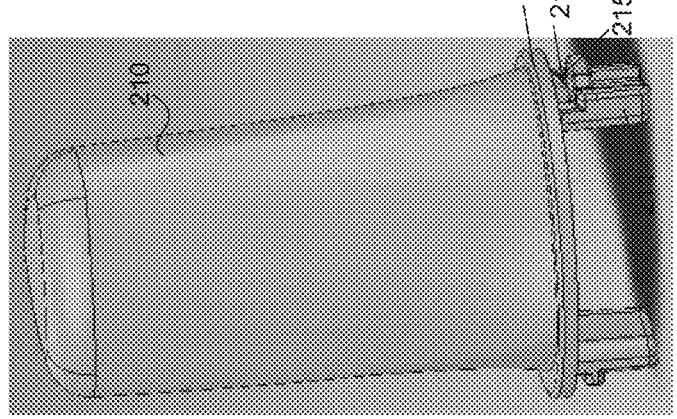
FIG. 8
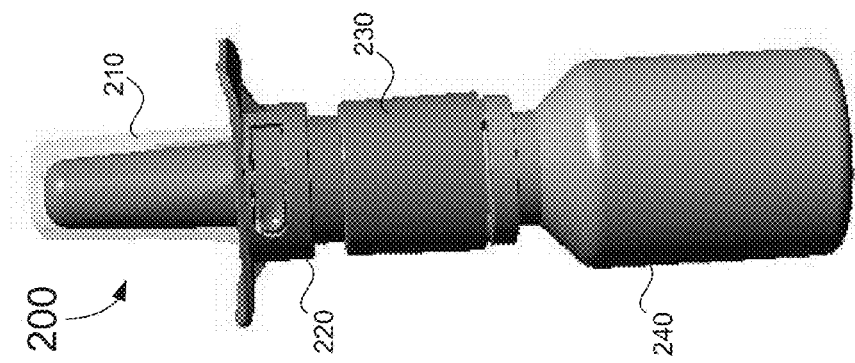
FIG. 7

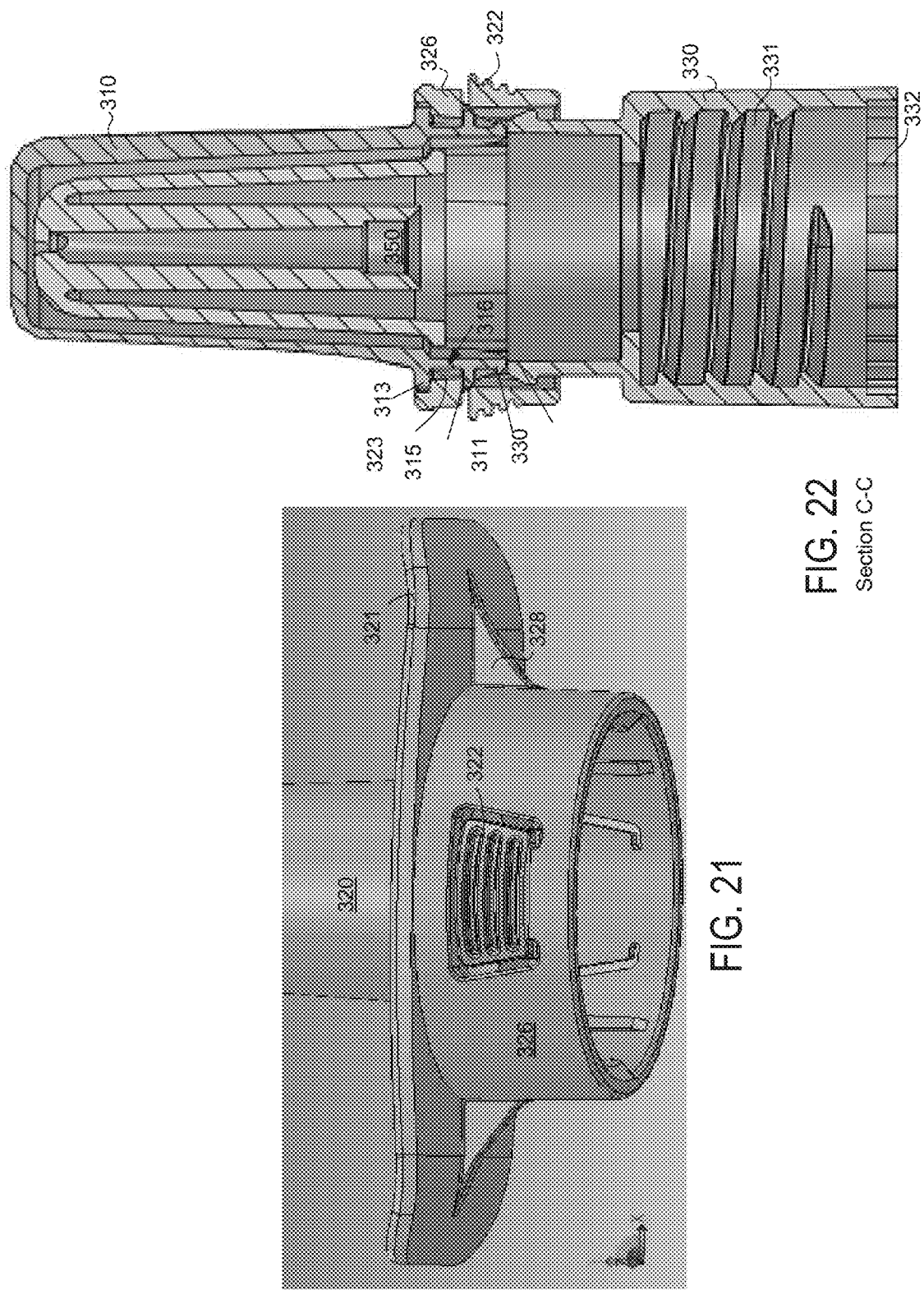

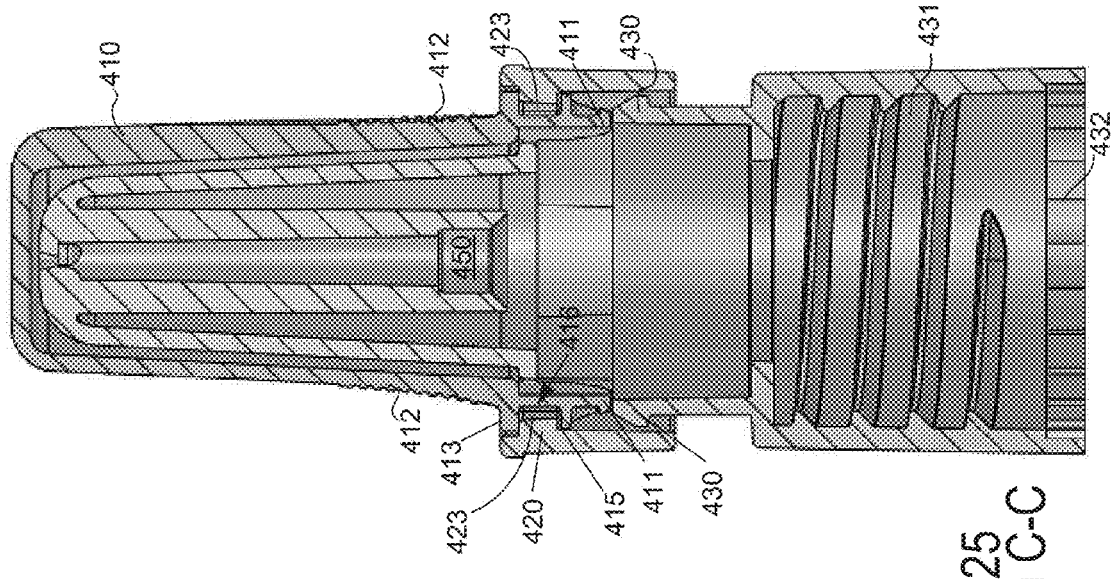
FIG. 25 Section C-C
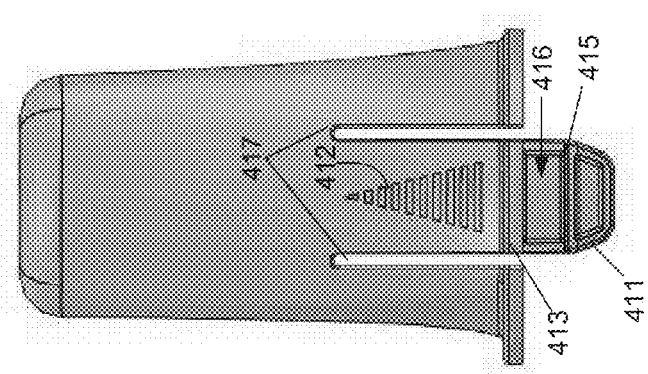
FIG. 24
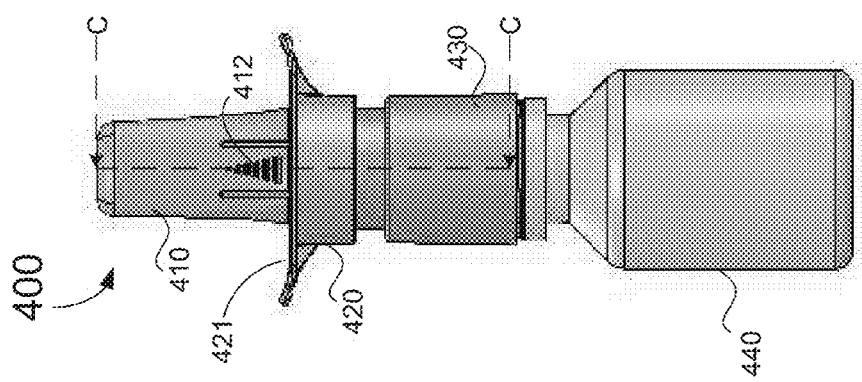
FIG. 23

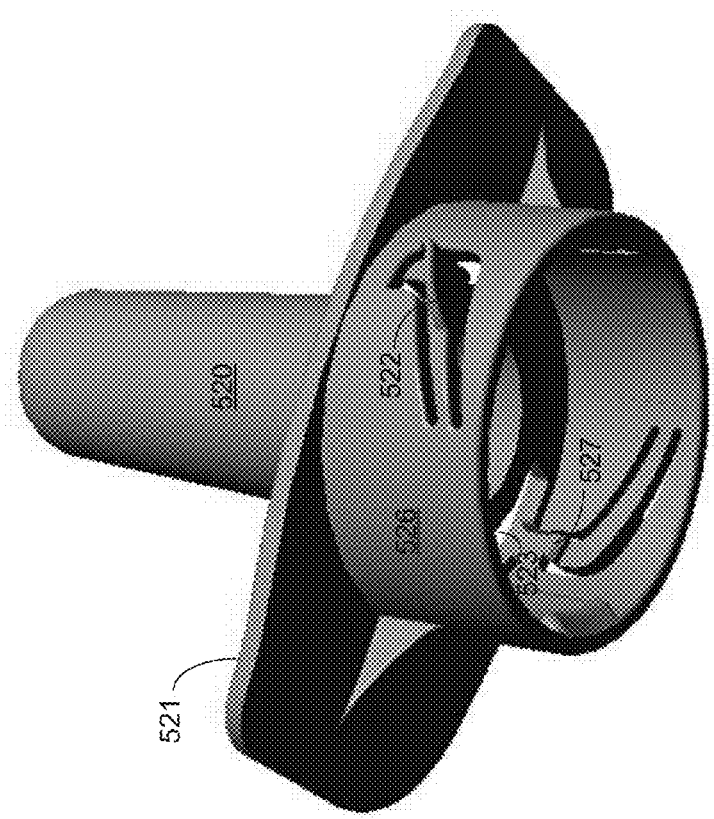
FIG. 28
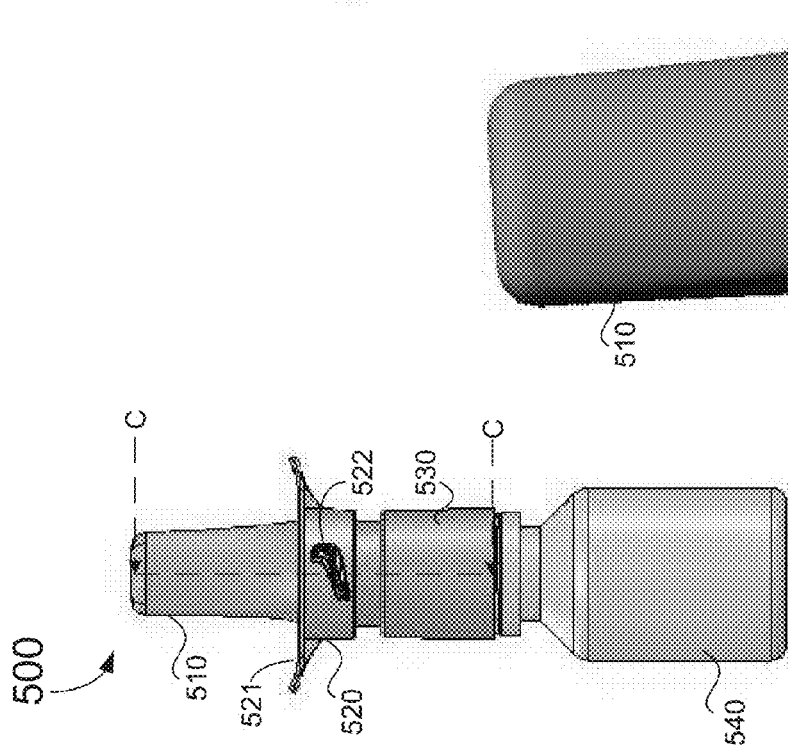
FIG. 27
FIG. 26

Section C-C

Section C-C

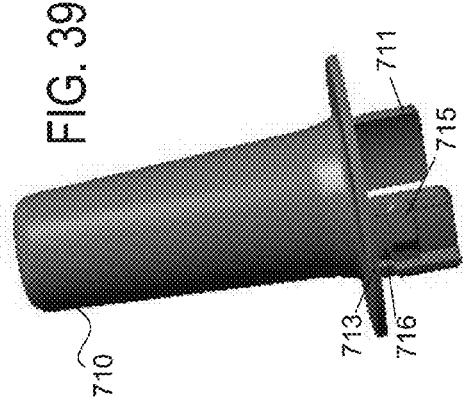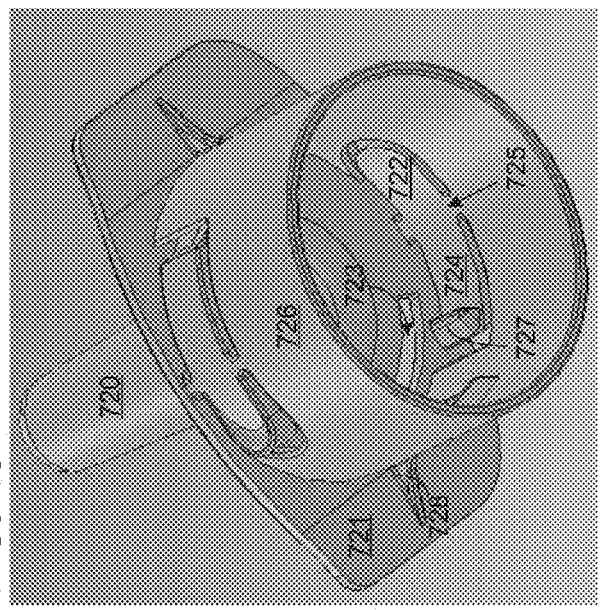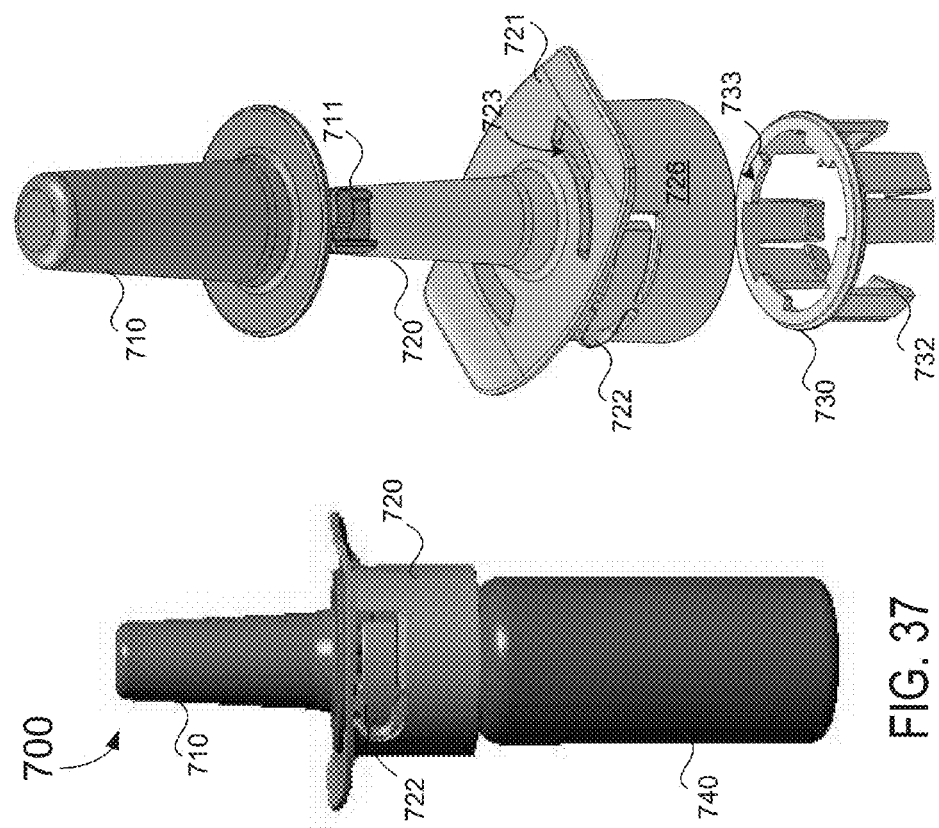

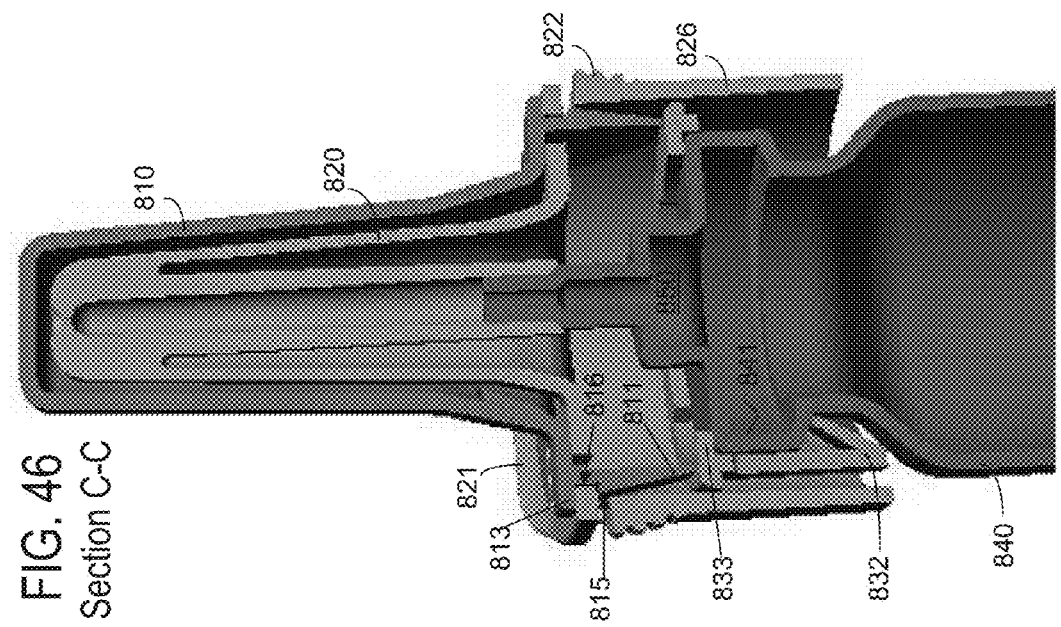
FIG. 46 Section C-C
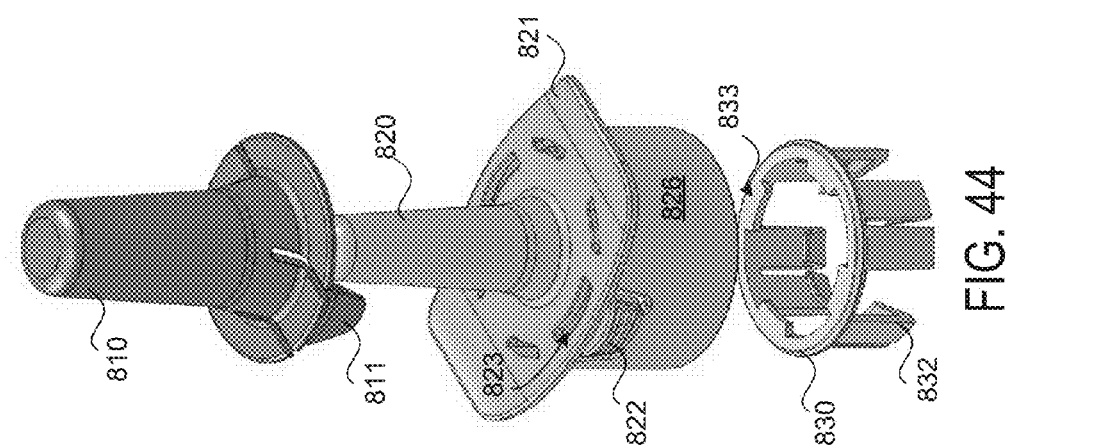
FIG. 44
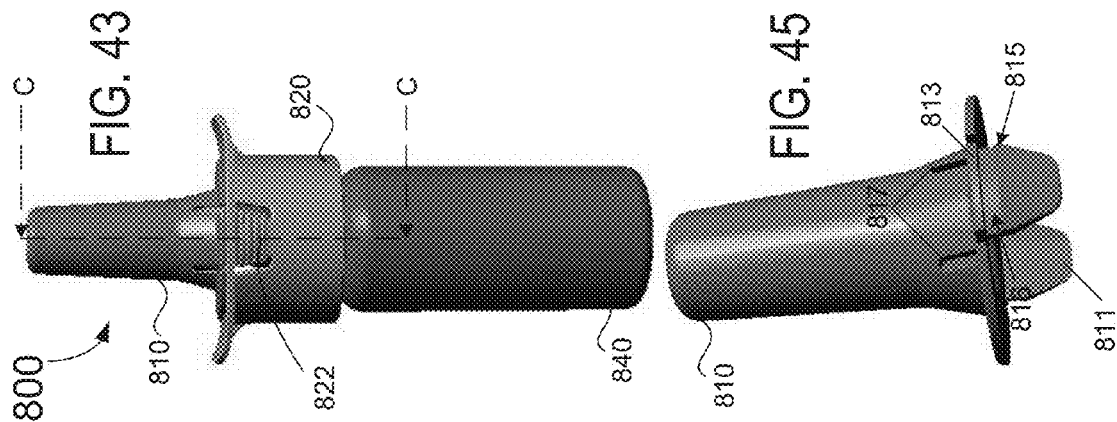
FIG. 43
FIG. 45

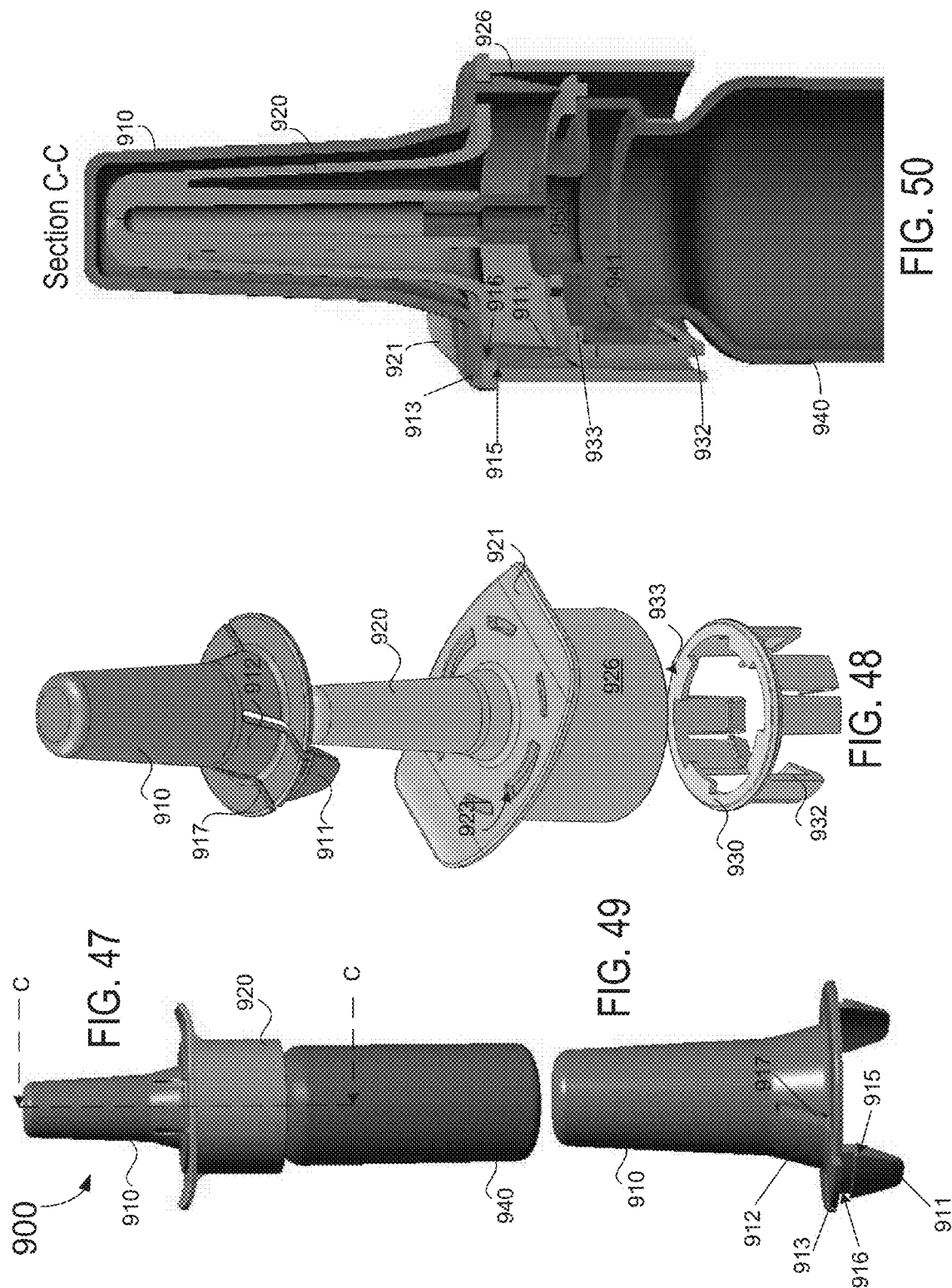

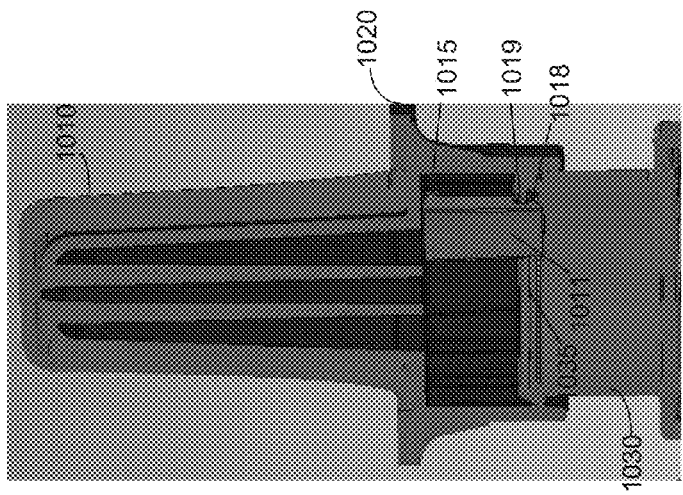
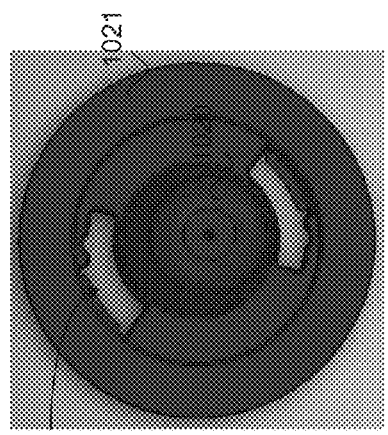
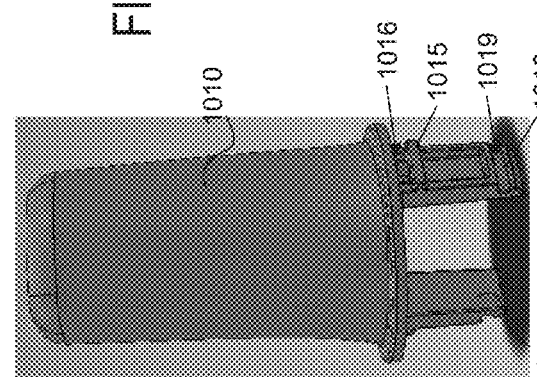
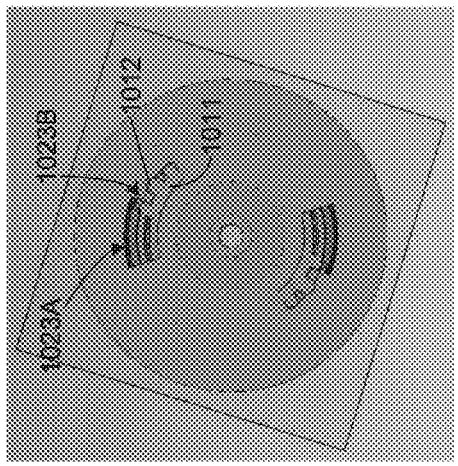
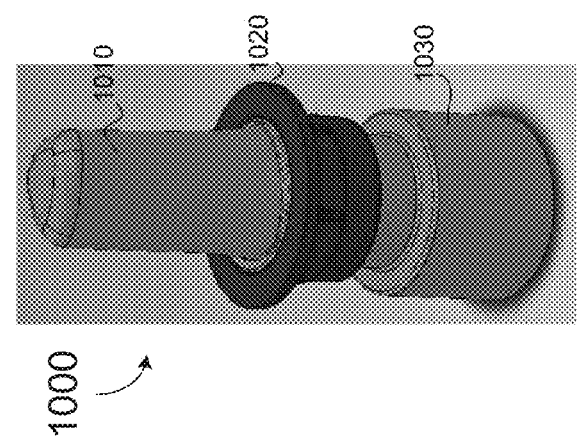
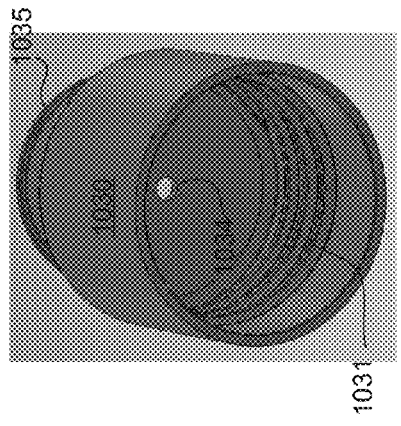

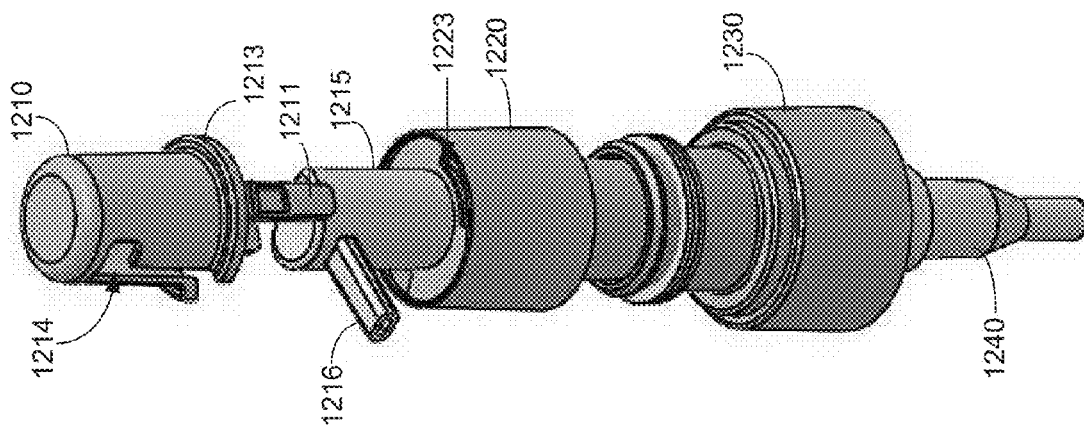
FIG. 67
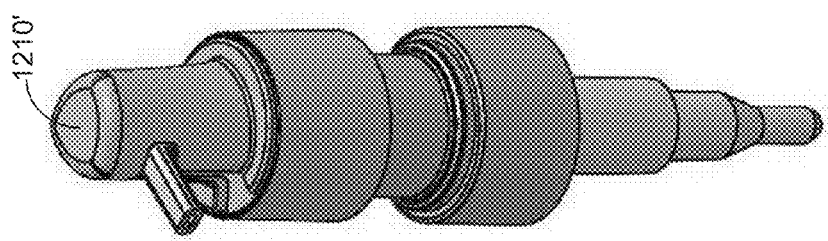
FIG. 66
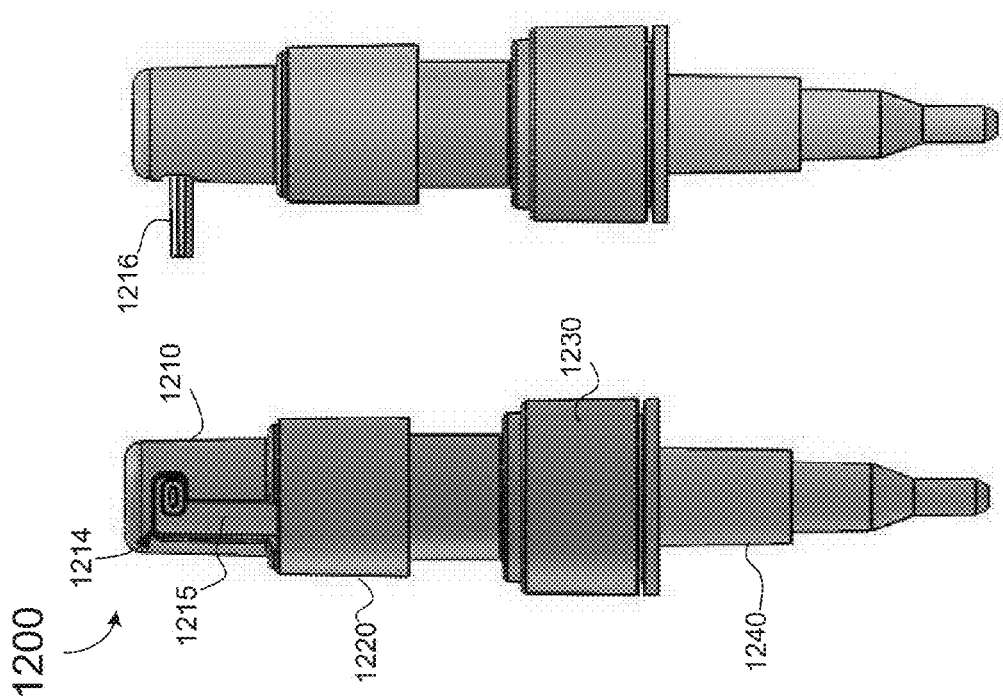
FIG. 65
FIG. 64

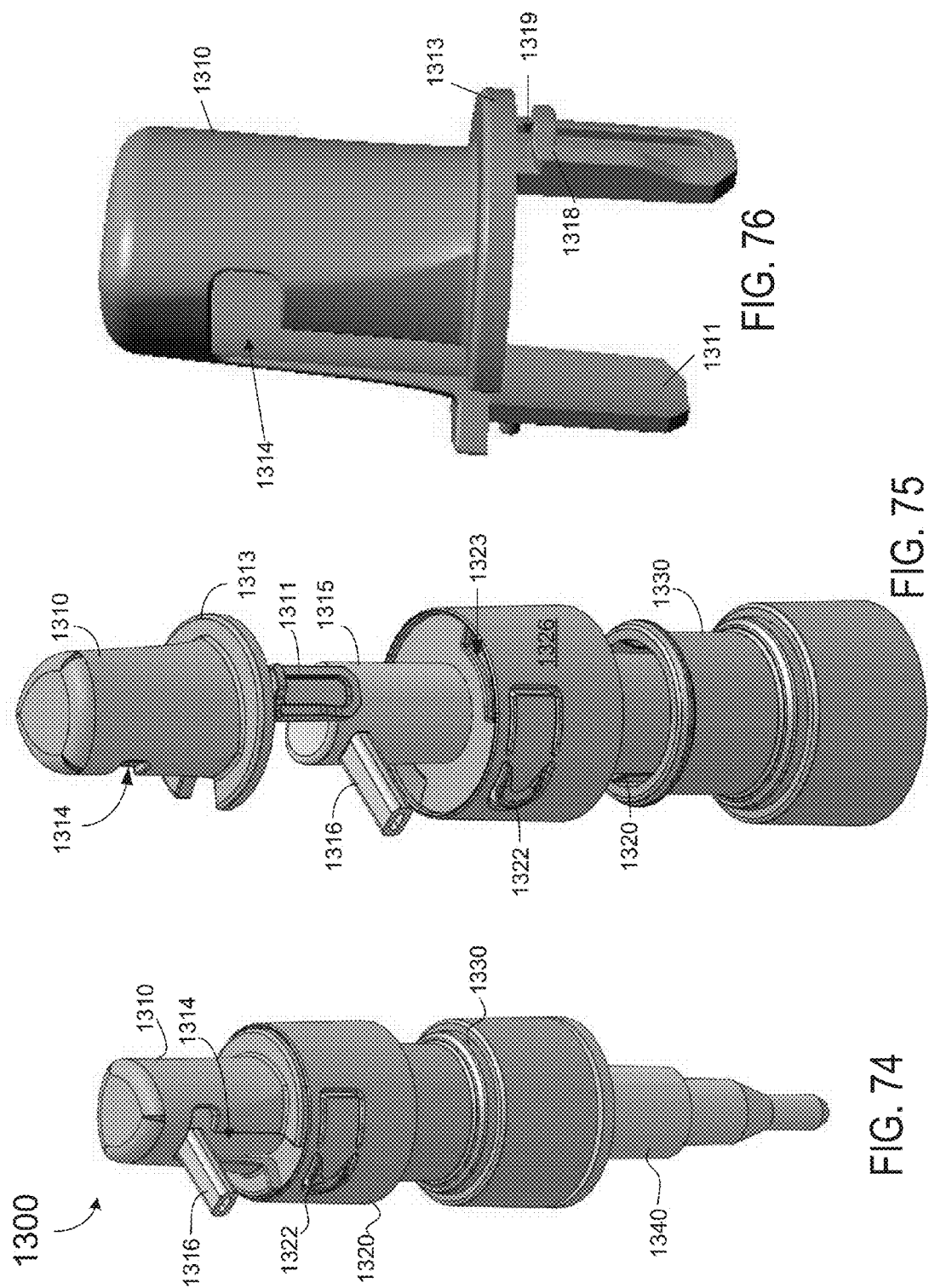

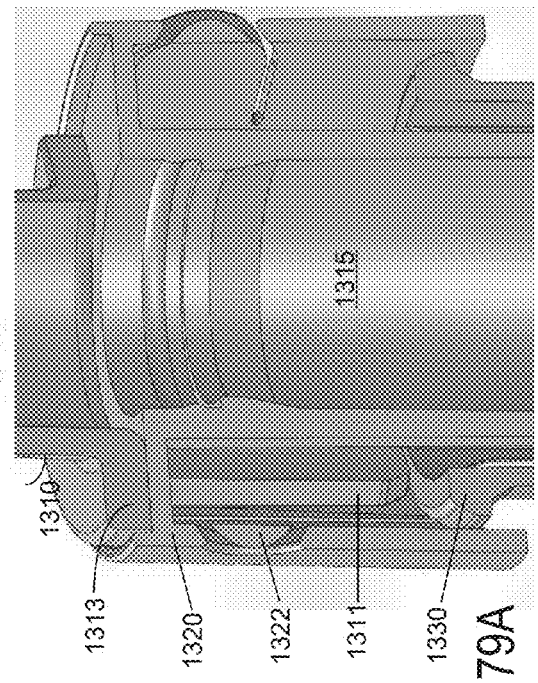
FIG. 79
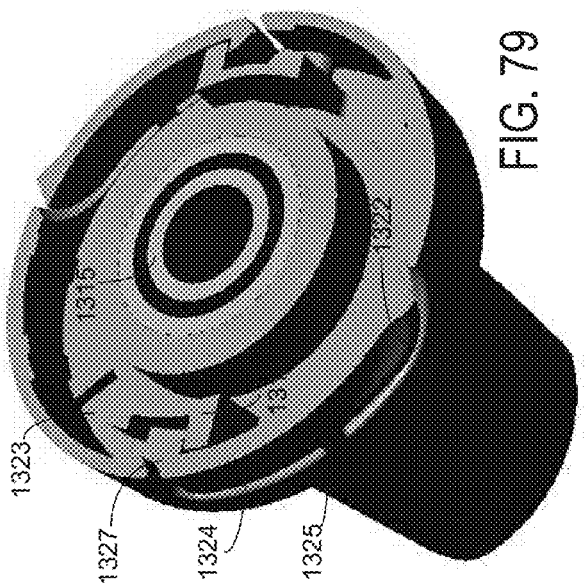
FIG. 79A
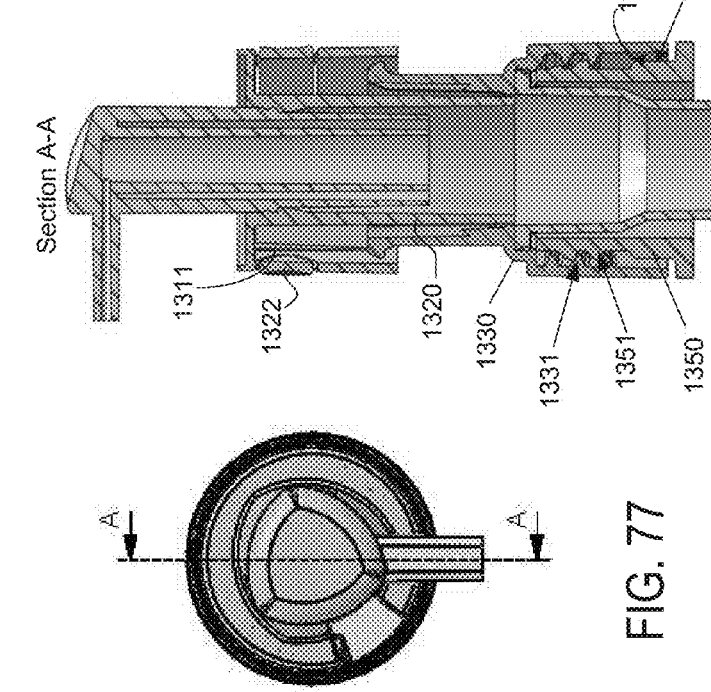
FIG. 78
FIG. 77

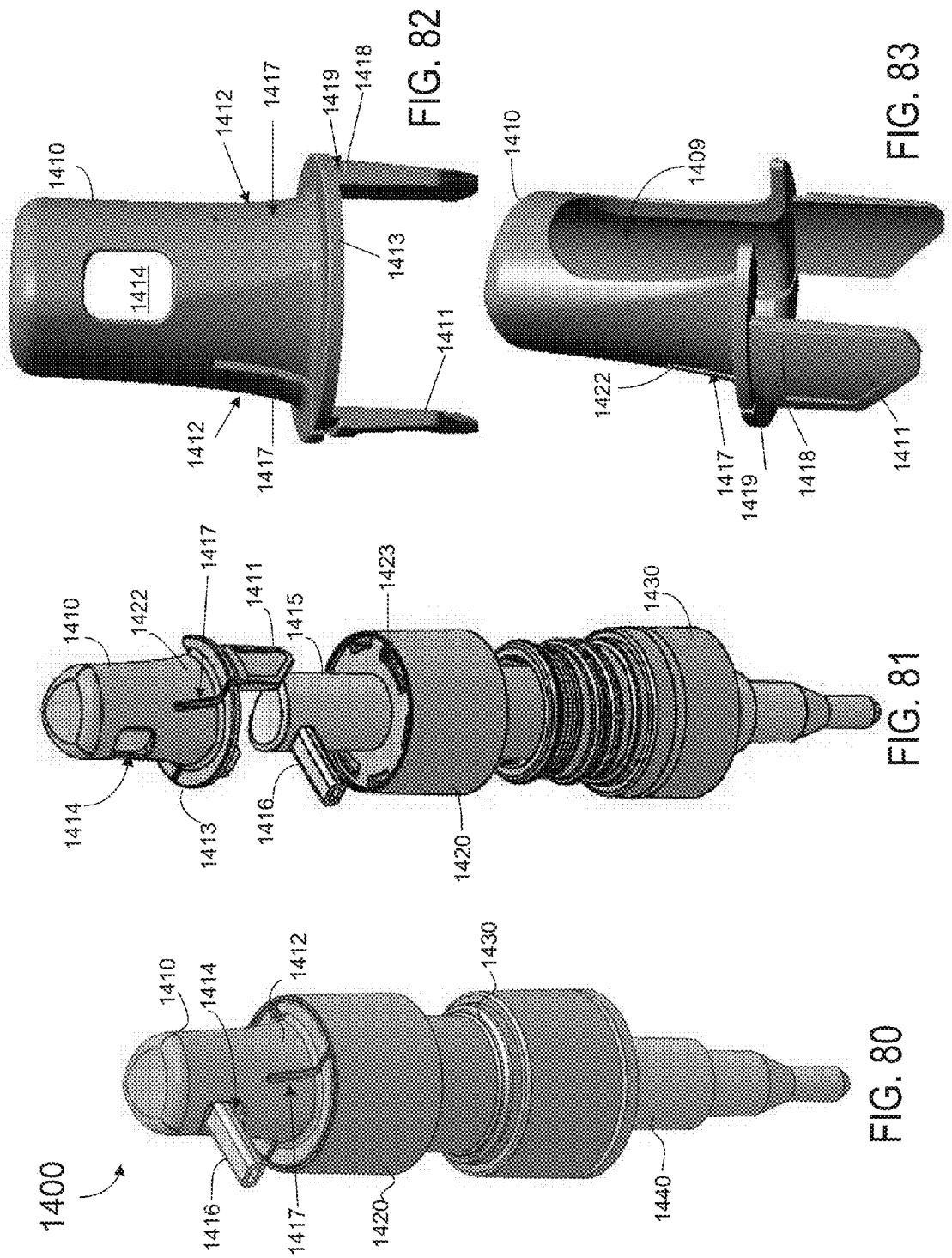

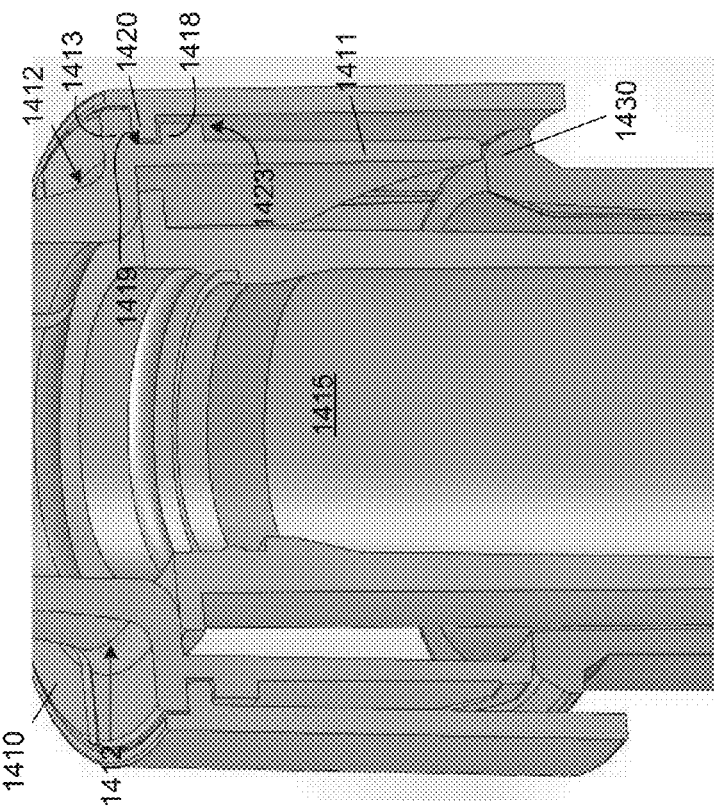
FIG. 86
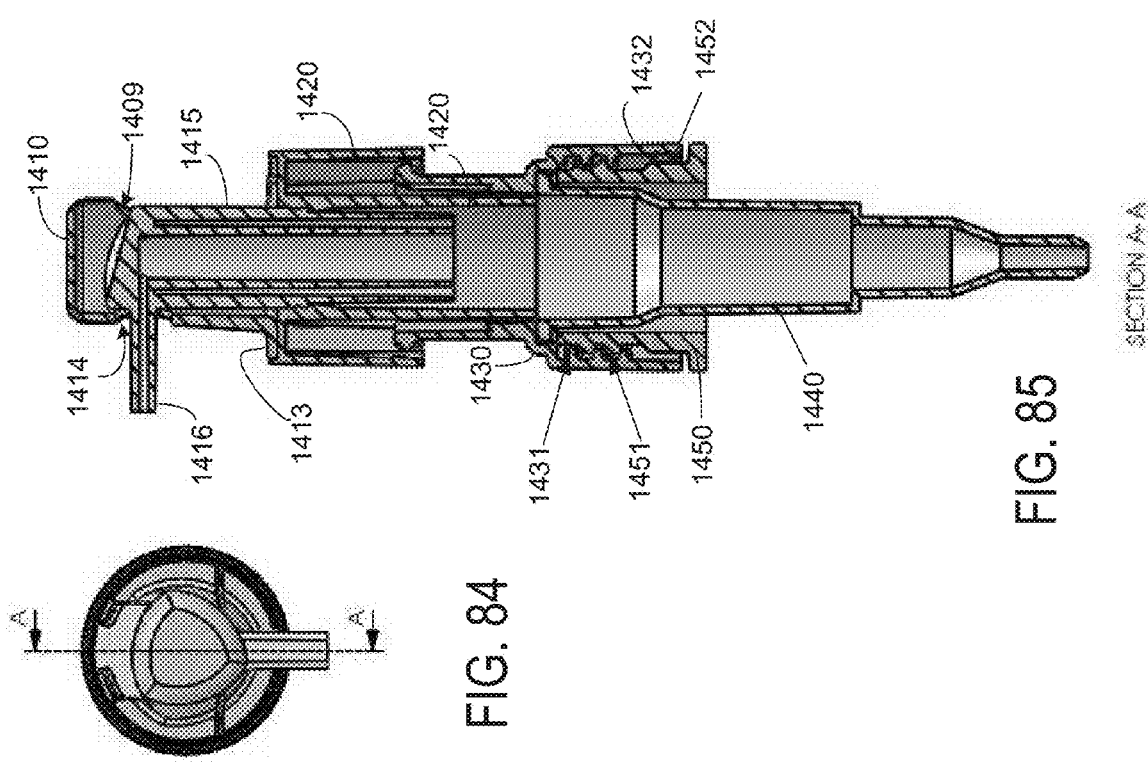
FIG. 84
FIG. 85
SECTION A-A

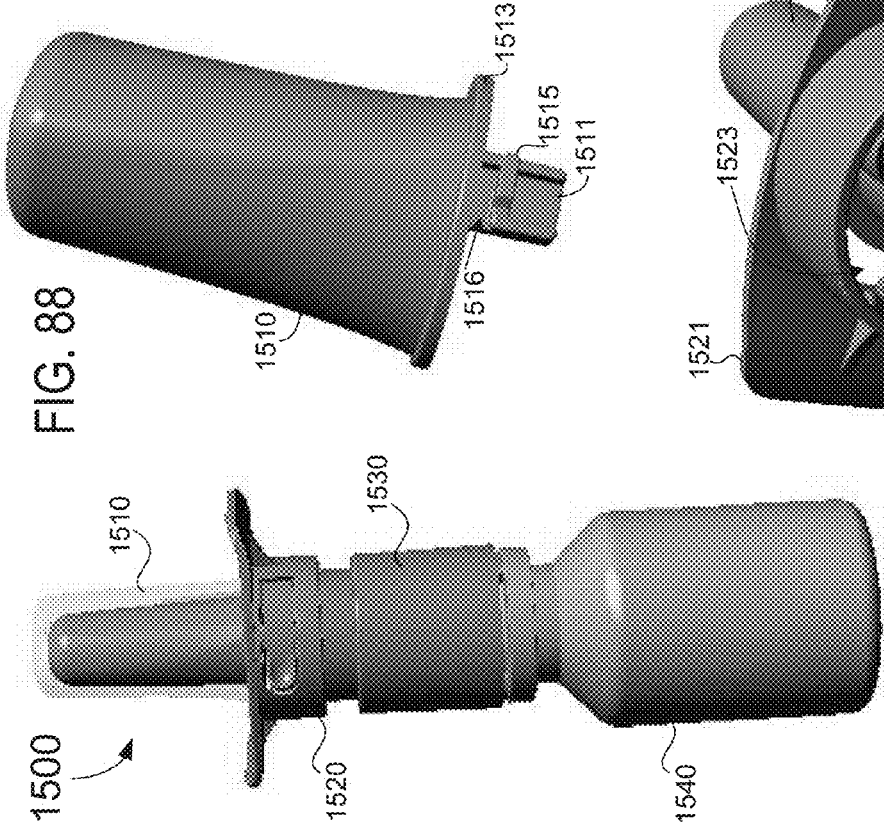
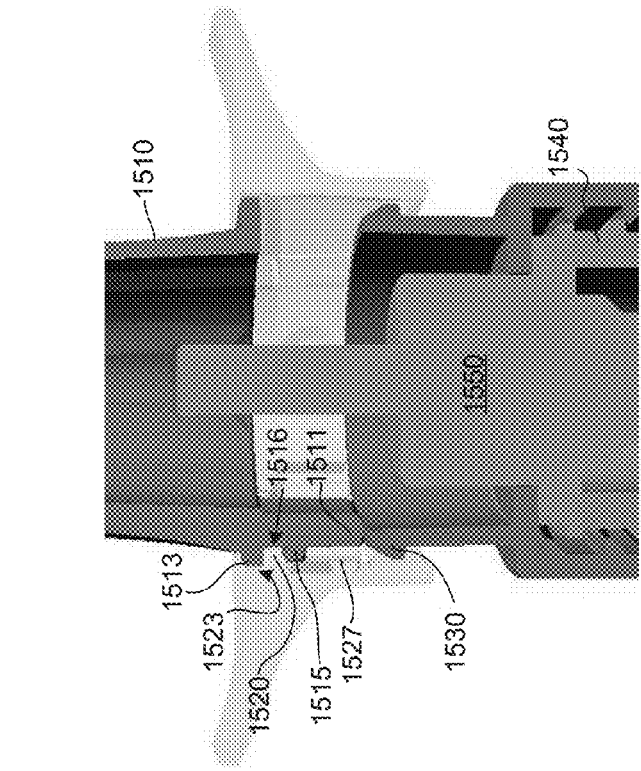
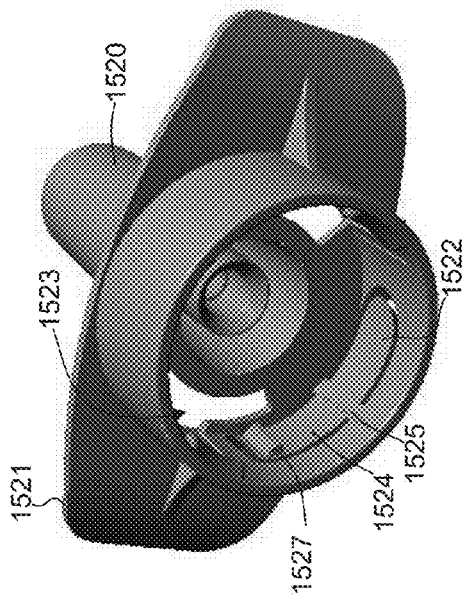
FIG. 87
FIG. 88
FIG. 89
FIG. 90

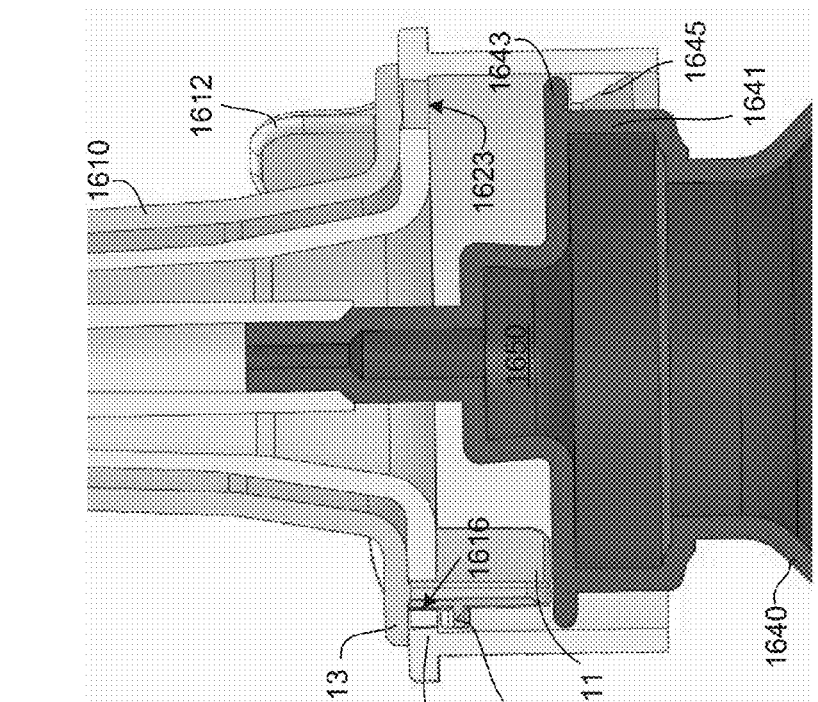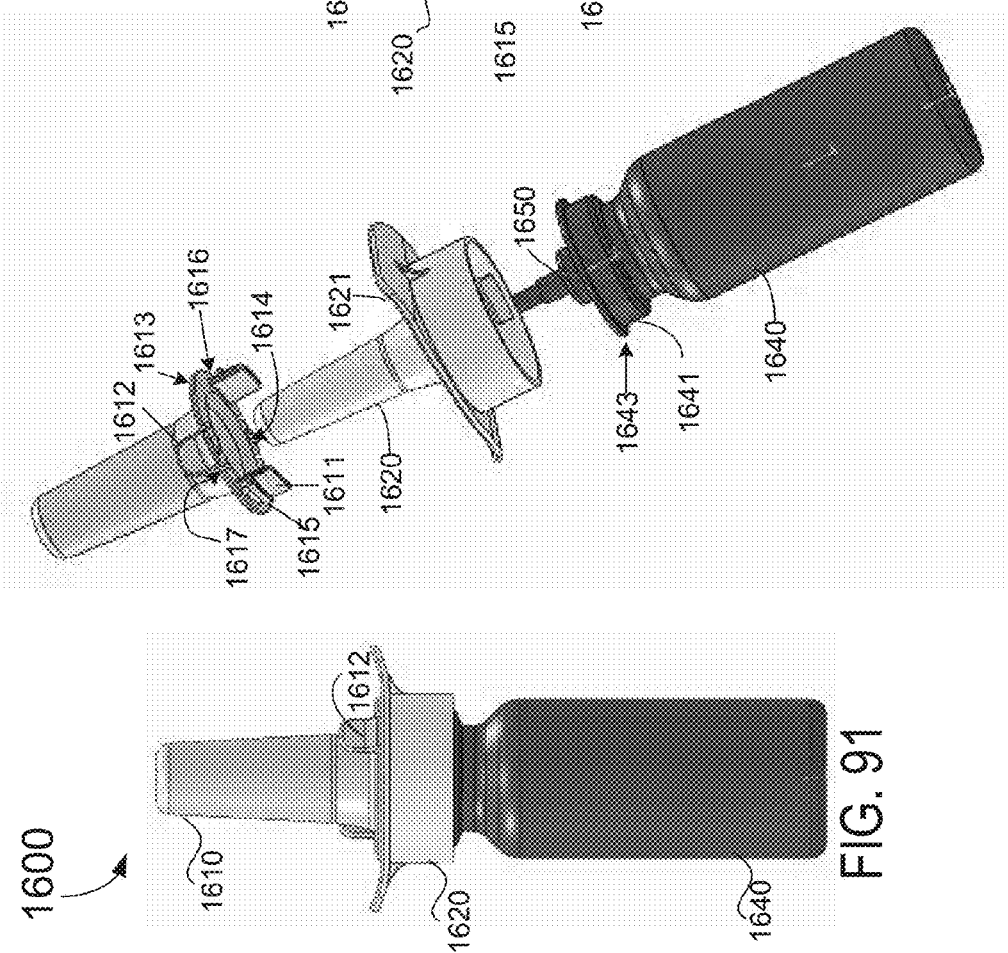

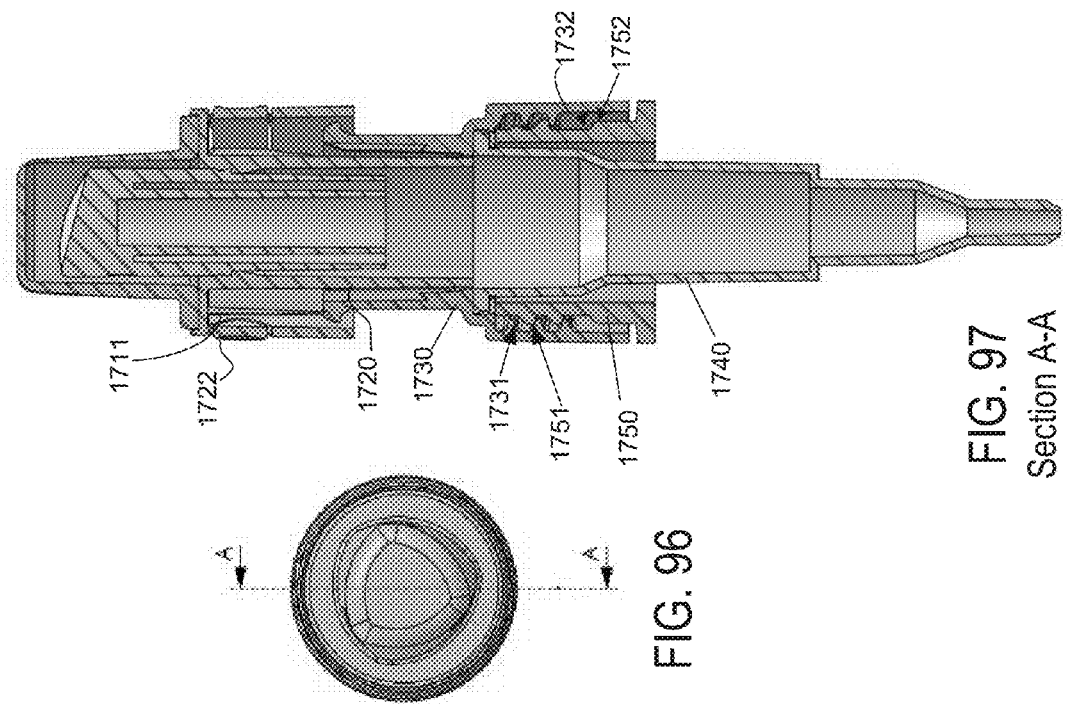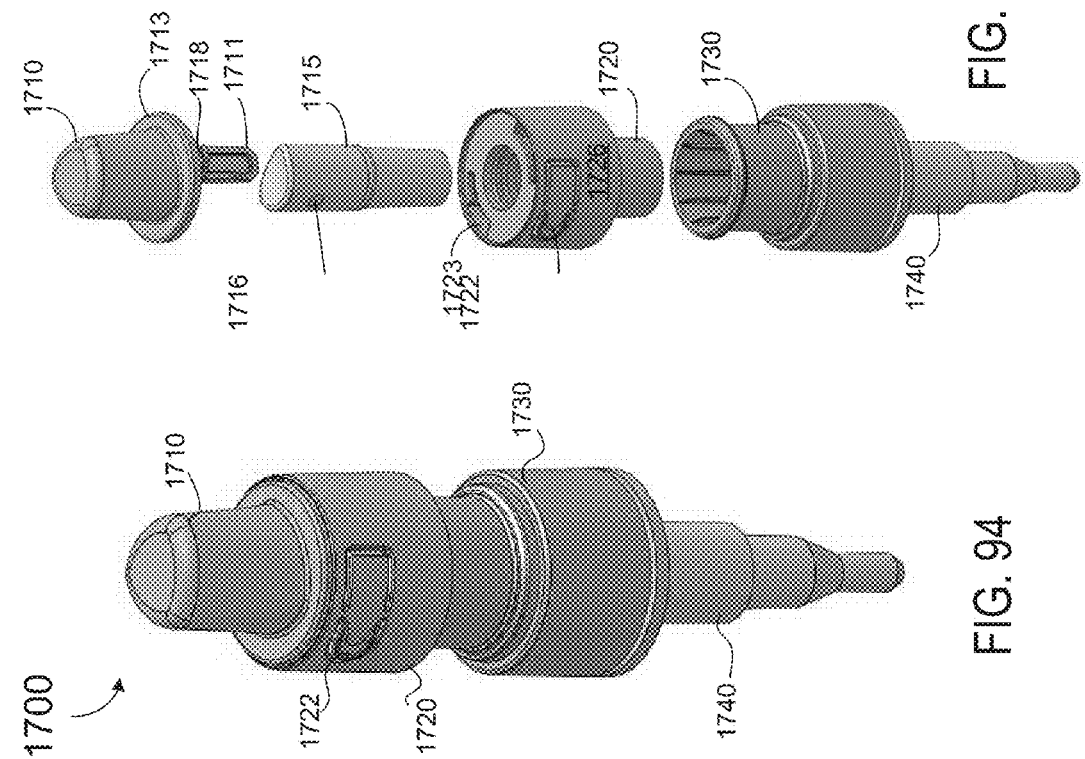

CHILD-RESISTANT CLOSURE SYSTEMS FOR CONTAINERS

CROSS-REFERENCE TO RELATED APPLICATION

The present application is a continuation of and claims priority to U.S. patent application Ser. No. 14/216,595, filed Mar. 17, 2014, which in turn claims the benefit under 35 U.S.C. §119(e) of U.S. Provisional Patent Application No. 61/802,060 to the inventors, filed Mar. 15, 2013, the entire contents of which are hereby incorporated by reference herein.

BACKGROUND

1. Field

Example embodiments in general relate to child-resistant closure systems for containers.

2. Related Art

The Consumer Product Safety Commission ("CPSC") proposed a rule in early 2012 to require child-resistant ("CR") packaging for any over-the-counter or prescription product containing the equivalent of 0.08 milligrams or more of an imidazoline, a class of drugs that includes tetrahydrozoline, naphazoline, oxymetazoline, and xylometazoline, in a single package. Imidazolines are a family of drugs that are vasoconstrictors indicated for nasal congestion and/or ophthalmic irritation. Products containing imidazolines can cause serious adverse reactions, such as central nervous system ("CNS") depression, decreased heart rate, and depressed ventilation in children treated with these drugs or who accidentally ingest them. Based on the scientific data, the CPSC has preliminarily found that availability of 0.08 milligrams or more of an imidazoline in a single package, by reason of its packaging, is such that special packaging is required to protect children under 5 years old from serious personal injury or illness due to handling, using, or ingesting such a substance. The CPSC has taken this action under the Poison Prevention Packaging Act of 1970.

Accordingly, as it is expected that this rule will become law, manufacturers will be required to develop child-resistant closure (CRC) systems for their nasal pump sprayers and eye-dropper dispenser products (such as Visine®), as each of these products contain the equivalent of 0.08 milligrams or more of an imidazoline. In doing so, one goal is to ensure that the newly developed dispensers are robust enough to prevent children five years old and under from being able to inadvertently open the bottle to use or ingest the contents, while still being "senior friendly" to mature adults.

Moreover, the same child-resistant principals as to be applied to nasal sprayers and eye-dropper (squeeze) bottles so as to comply with impending CR packaging regulations, could also be made applicable to other fields of fluid dispenser/packaging. For example, little or no thought has be given to developing CRC systems for consumer fluid pump dispensers having a viscosity generally higher than that of water or water-based medicinal fluids, such as those dispensers holding lotions, shampoos, baby oils, and paints.

SUMMARY

An example embodiment is directed to a child-resistant closure system for a pump sprayer. The system includes a cap having a rim at its lower end and including a pair of legs, each leg in opposite relation to one another and extending downward from the rim, each leg tapered and including a rib thereon which extends outward from the side of the leg, with an undercut provided between each rib and the rim of the cap. The system includes a dispensing tip configured to receive the cap thereon, a lower end of the dispensing tip including a pair of finger-depressing shoulders in opposite relation to one another and extending horizontally outward from the dispensing tip, each shoulder including a slot therein that is configured to receive a corresponding leg of the cap therethrough for locking the cap to the dispensing tip, with a cylindrical collar provided beneath the shoulders as the bottom end of the dispensing tip, the collar including a pair of buttons in opposite relation to one another on a vertical facing of the collar, the buttons configured to be simultaneously actuated to release the legs from interior structure within the dispensing tip so as to remove the cap off of the dispensing tip. The system includes a cylindrical base having its upper end secured to the collar of the dispensing tip and its lower end secured to a dispenser bottle which contains fluid, the dispensing tip and base housing a sprayer pump unit therein which partly extends into the dispenser bottle interior and which is actuated by depressing the shoulders on the dispensing tip to spray the fluid within the dispenser bottle. With the cap in place on the dispensing tip, the legs extend downward through the slots in the shoulders to contact the top of the base, with interior structure within the dispensing tip engaged in the undercuts provided between the ribs of the legs and the rim of the cap so as to allow for the sprayer pump unit to be locked out from operation. To release the cap so as to permit actuation of the sprayer pump unit via the shoulders, the buttons on the collar are pressed simultaneously to deflect the legs inward and off of the base, which also deflects the corresponding ribs on the legs away from interior structure within the dispensing tip, so that the cap with its legs is drawn up through the slots in the shoulders and off of the dispensing tip.

BRIEF DESCRIPTION OF THE DRAWINGS

Example embodiments will become more fully understood from the detailed description given herein below and the accompanying drawing, wherein like elements are represented by like reference numerals, which are given by way of illustration only and thus are not limitative of the example embodiments herein.

FIG. 7 is a front view of a child-resistant closure system for a pump sprayer according to another example embodiment.

FIG. 8 is a perspective view of a cap according to the system of FIG. 7.

FIG. 9 is a front perspective view of a dispensing tip according to the system of FIG. 7.

FIG. 10 is a top view of the dispensing tip shown in FIG. 9.

FIG. 21 is a close-up view of a lower portion of a dispensing tip according to the system of FIG. 17.

FIG. 22 is sectional view C-C taken from FIG. 17.

FIG. 23 is a front view of a child-resistant closure system for a pump sprayer according to another example embodiment.

FIG. 24 is a front view of a cap according to the system of FIG. 23.

FIG. 25 is sectional view C-C taken from FIG. 23.

FIG. 26 is a front view of a child-resistant closure system for a pump sprayer according to another example embodiment.

FIG. 27 is a perspective view of a cap according to the system of FIG. 26.

FIG. 28 is a front perspective view of a dispensing tip according to the system of FIG. 26.

FIG. 37 is a front view of a child-resistant closure system for a pump sprayer according to another example embodiment.

FIG. 38 is an exploded view of selected components of the system of FIG. 37.

FIG. 39 is a perspective view of a cap according to the system of FIG. 37.

FIG. 40 is a front rotated view of the dispensing tip of FIG. 38.

FIG. 43 is a front view of a child-resistant closure system for a pump sprayer according to another example embodiment.

FIG. 44 is an exploded view of selected components of the system of FIG. 43.

FIG. 45 is a perspective view of a cap according to the system of FIG. 43.

FIG. 46 is sectional view C-C taken from FIG. 43.

FIG. 47 is a front view of a child-resistant closure system for a pump sprayer according to another example embodiment.

FIG. 48 is an exploded view of selected components of the system of FIG. 47.

FIG. 49 is a perspective view of a cap according to the system of FIG. 47.

FIG. 50 is sectional view C-C taken from FIG. 47.

FIG. 51 is a perspective view of a child-resistant closure system for a pump sprayer according to another example embodiment.

FIG. 52 is a perspective view of a cap according to the system of FIG. 51.

FIG. 53 is a top view of the dispensing according to the system of FIG. 51.

FIG. 54 is a bottom perspective view of a base according to the system of FIG. 51.

FIG. 55 is a portion of a cross-cut of the cap and dispensing tip in a bottom view to show positions of the legs in the slots in a locked position.

FIG. 56 is a portion of a sectional view of the system in the yz-plane to illustrate a locked condition.

FIG. 64 is a front view of a child-resistant closure system for a pump assembly according to another example embodiment.

FIG. 65 is a side view of the assembly of FIG. 64.

FIG. 66 is a perspective view of the assembly of FIG. 64 with a different pump cap.

FIG. 67 is an exploded view of selected components of the system of FIG. 64.

FIG. 74 is a front view of a child-resistant closure system for a pump assembly according to another example embodiment.

FIG. 75 is an exploded view of selected components of the system of FIG. 74.

FIG. 76 is a perspective view of the pump cap of the system.

FIG. 77 is a top view of the dispenser according to the system.

FIG. 78 is sectional view A-A taken from FIG. 77.

FIG. 79 is a portion of a sectional view of the dispenser and legs in the xz-plane from a bottom viewpoint with selected components removed to illustrate a locked condition.

FIG. 79A is a sectional view taken in the xy plane of a portion of the system to show a locked condition thereof.

FIG. 80 is a perspective view of a child-resistant closure system for a pump assembly according to another example embodiment.

FIG. 81 is an exploded view of selected components of the system of FIG. 80.

FIG. 82 is a front view of the pump cap of the system.

FIG. 83 is a rear perspective view of the cap of FIG. 82.

FIG. 84 is a top view of the system of FIG. 80.

FIG. 85 is sectional view A-A taken from FIG. 84.

FIG. 86 is a sectional view taken in the xy plane of a portion of the system to show a locked condition thereof.

FIG. 87 is a front view of a child-resistant closure system for a pump sprayer according to another example embodiment.

FIG. 88 is a perspective view of a cap according to the system of FIG. 87.

FIG. 89 is a bottom perspective view of a dispensing tip according to the system of FIG. 87.

FIG. 90 is a portion of a sectional view taken of the system in the xy-plane to show a locked condition.

FIG. 91 is a perspective view of a child-resistant closure system for a pump sprayer according to another example embodiment.

FIG. 92 is an exploded view of the system of FIG. 91.

FIG. 93 is a portion of a sectional view taken of the system in the xy-plane to show a locked condition.

FIG. 94 is a front view of a child-resistant closure system for a pump assembly according to another example embodiment.

FIG. 95 is an exploded view of selected components of the system of FIG. 94.

FIG. 96 is a top view of the dispenser according to the system.

FIG. 97 is sectional view A-A taken from FIG. 96.

DETAILED DESCRIPTION

Figure 1:
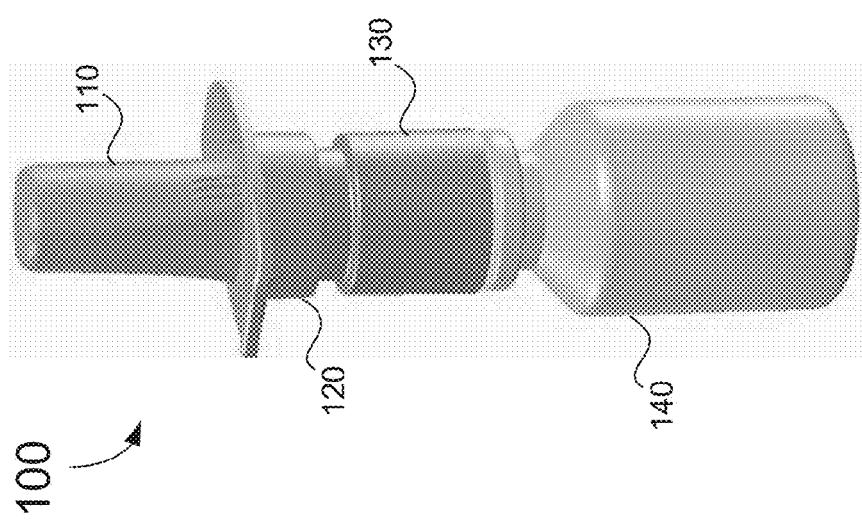
FIG. 1 is a perspective view of a child-resistant closure system for a pump sprayer according to an example embodiment.

FIG. 1 is a perspective view of a child-resistant closure system for a pump sprayer according to an example embodiment. The child-resistant closure (CRC) system 100 includes a cap 110, a dispensing tip 120 and a base 130. Each of the cap 110, dispensing tip 120 and base 130 may be injection molded or extruded or otherwise formed of a suitable plastic material, as is known. The cap 110 is 3-sided to minimize rolling and avoid losing the cap 110. The base 130 has interior grooves or threads for coupling it to a threaded member on dispenser bottle 140 which holds the medicinal fluid therein. The base 130 and dispensing tip 120 also enclose a sprayer pump unit 150 (not shown) which partly extends into the dispenser bottle 140 interior.

In an example, the CRC system 100 described here and child-resistant based embodiments to be described hereafter may be applicable, but not limited to: single or multi-dose dispensers such as nasal sprayers, ocular sprayers, dermal sprayers, misters, aerators, airless dispensers, air-use dispensers, spouted and non-spouted pump assemblies, and the like. The containers or dispensers foreseeable have applications in the healthcare, home and garden, beauty and food and beverage industries, thus the embodiments described herein are applicable to dispensers or containers configured for, but not limited to dispensing nasal medicine, sunscreens, food products, paints and protectants, deodorants, insect repellants, sealed breath fresheners, ear medicine, dermal medicine, lotions, fragrances, air fresheners, spray starches, oxygen, insecticides, fungicides, herbicides, rodenticides, spray oils, talcs, and spray food stuffs. Further, the CRC systems can be varied in size and applied as a platform to handle any desired viscosity of fluid.

Figure 2:
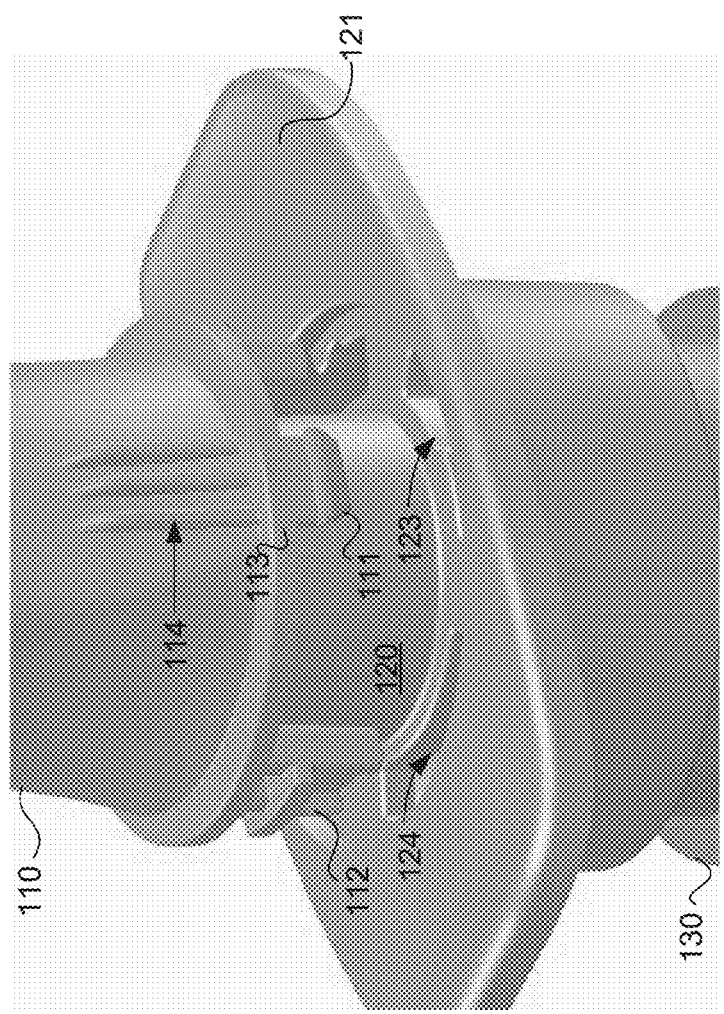
FIG. 2 is an enlarged view of a portion of an interface between cap and dispensing tip to show selected components thereof.

FIG. 2 is an enlarged view of a portion of an interface between cap and dispensing tip to show selected components thereof. The dispensing tip 120 includes finger depressing shoulders 121 on which is formed a plurality of slots 123 and 124. Slots 123 are adapted to receive corresponding hooks 111 which extend from the bottom rim 113 of cap 110. Slots 124 are adapted to receive extending legs 112 of the cap 110. As will be seen, the hooks 111 and legs 112 prevent actuation of shoulders 121 in a locked condition, with the hooks 111 preventing removal of the cap 110 whether or not the cap 110 is locked or unlocked to the dispensing tip 120.

Figure 4:
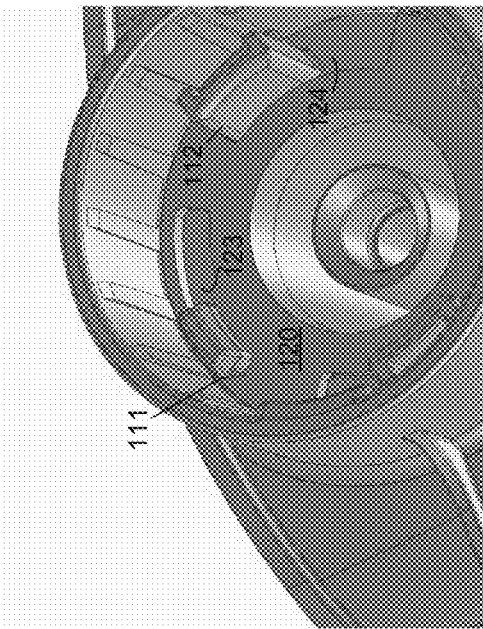
FIG. 4 is a portion of a sectional view of the underside of the dispensing tip in the xz-plane with selected components removed to illustrate a locked condition.
Figure 5:
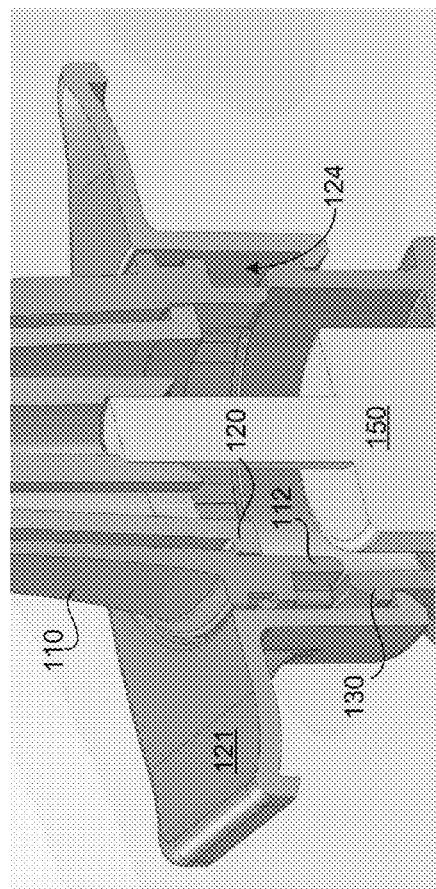
FIG. 5 is a portion of a sectional view of the system in the xy-plane to illustrate a locked condition.
Figure 3A:
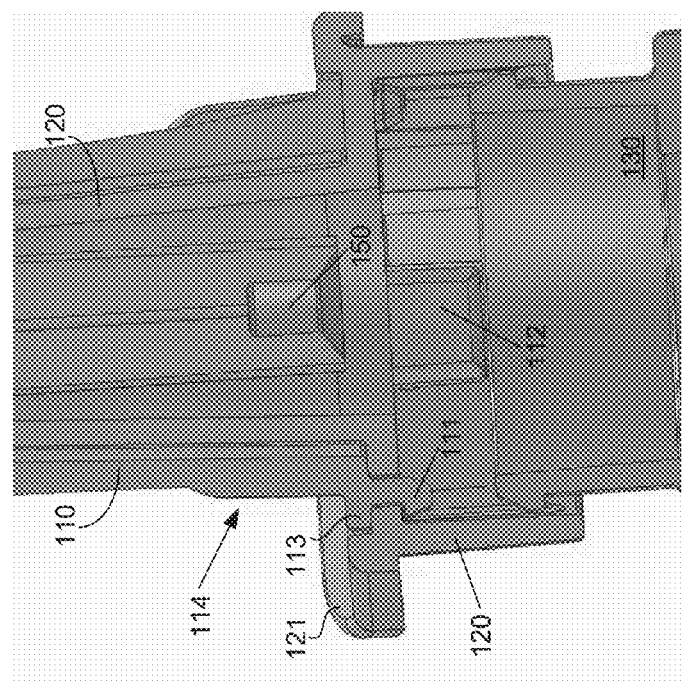
FIG. 3A is a portion of a sectional view of the system in the yz-plane to illustrate a locked condition.

FIG. 3A is a portion of a sectional view of the system in the yz-plane to illustrate a locked condition, FIG. 4 is a portion of a sectional view of the underside of the dispensing tip in the xz-plane with selected components removed to illustrate a locked condition, and FIG. 5 is a portion of a sectional view of the system in the xy-plane to illustrate an locked condition. Referring to FIGS. 3A-5, when the cap 110 is inserted into the slots 123, 124, the hooks 111 snap fit into slots 123 and lock, such that a hook 111 and the rim 113 of cap 110 captures part of dispensing tip 120 around the edge of slot 123, as can be seen in both FIGS. 3 and 4. As shown in FIG. 5, the legs 112 extend all the way down through slots 124 to terminate against base 130. Accordingly, depression of shoulders 121 to activate sprayer pump unit 150 is not possible; operation is locked out.

Figure 6:
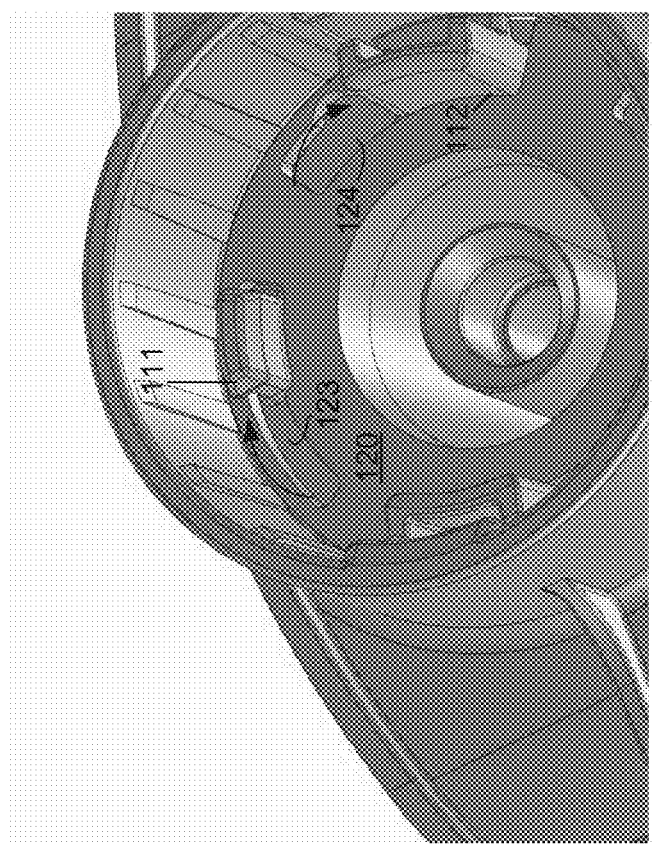
FIG. 6 is a portion of a sectional view of the underside of the dispensing tip in the xz-plane with selected components removed to illustrate an unlocked condition.
Figure 3B:
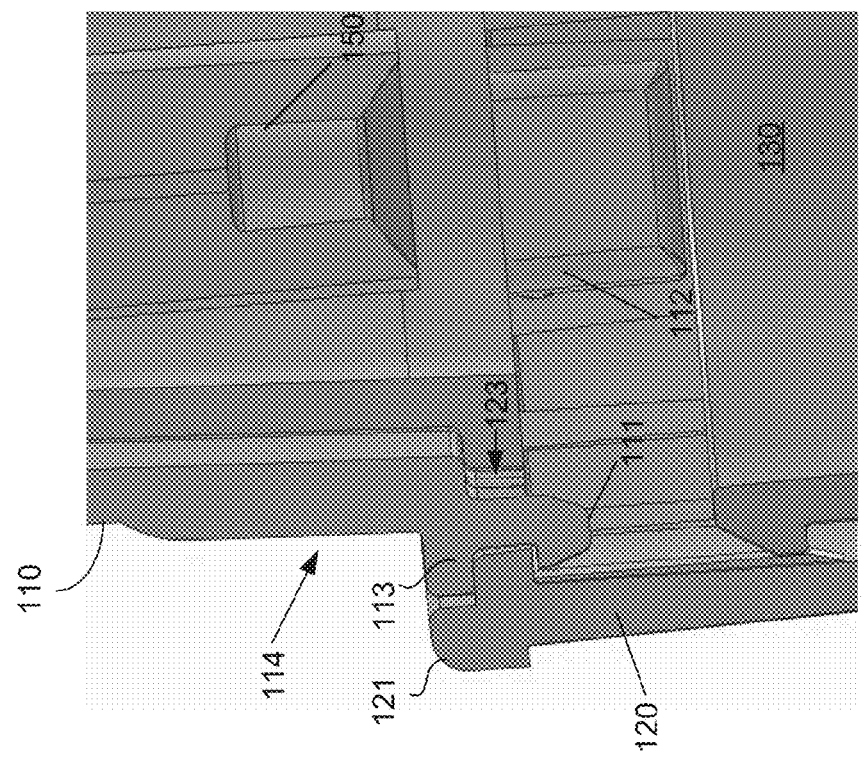
FIG. 3B is a portion of a sectional view of the system in the yz-plane to illustrate an unlocked condition

FIG. 3B is a portion of a sectional view of the system in the yz-plane to illustrate an unlocked condition, and FIG. 6 is a portion of a sectional view of the underside of the dispensing tip in the xz-plane with selected components removed to illustrate an unlocked condition. To remove the cap 110, a user needs to rotate the cap 110, as best seen in FIG. 6. This aligns the hooks 111 and legs 112 in the wider portions of their slots 123 and 124. However, although the cap 110 is loose, the hooks 111 are still retained to the inner lip surface of dispensing tip 120. In order to fully remove the cap 110 and permit pump actuation, one must squeeze both ribbed members 114 on the outer surface of cap 110, simultaneously. The ribbed members 114 are seen best in FIG. 2. By squeezing both ribbed members 114 simultaneously, the hooks 111 will deflect inward into the open larger slot space of slot 123, permitting cap 110 removal.

Thus, when cap 110 is in either the "locked" or "unlocked" position, the hooks 111 prevent the cap 110 from being removed, as they are always engaged under the surface of the dispensing tip 120. By placing the cap in the "unlocked" position and squeezing the sides of the cap 110 at the ribbed members 114, the hooks 111 are allowed to disengage and the cap 110 can be removed. Unlike locking caps which are "squeeze and twist", this design is "twist and squeeze. Additionally, because the hooks 111 snap into place when the cap 110 is installed, the end-user has the option of leaving the cap 110 unlocked, but it will still need to be squeezed to remove it, and it won't fall off. Moreover, as the shoulders 121 cannot be depressed with the cap 110 on, even loosely, it will still prevent accidental deployment.

FIG. 7 is a front view of a child-resistant closure system for a pump sprayer according to another example embodiment. The child-resistant closure (CRC) system 200 includes a cap 210, a dispensing tip 220 and a base 230. Each of the cap 210, dispensing tip 220 and base 230 may be injection molded or extruded or otherwise formed of a suitable plastic material, as is known. The cap 210 is 3-sided to minimize rolling and avoid losing the cap 210. The base 230 has interior grooves or threads for coupling it to a threaded member on dispenser bottle 240 which holds the medicinal fluid therein. The base 230 and dispensing tip 220 also enclose a sprayer pump unit 250 (not shown) which partly extends into the dispenser bottle 240 interior.

FIG. 8 is a perspective view of a cap according to the system of FIG. 7. Cap 210 has a pair of legs 211 extending downward on either side. Each leg 211 has a rib 215 separated from the rim 213 of the cap 210 by an undercut 216.

FIG. 9 is a front perspective view of a dispensing tip according to the system of FIG. 7, and FIG. 10 is a top view of the dispensing tip shown in FIG. 9. Dispensing tip 220 includes a pair of shoulders 221 that are used to depress the sprayer pump unit 250 within (not shown) under finger pressure, as is known. On either side is provided a pair of buttons 222 with reliefs 224 separated by a hinge 225 that acts as a cam when the button 222 is actuated by the user. A ramp 227 is position on the back side of each relief 224; this interfaces with each leg 211, once the legs 211 are inserted through slots 223 in the shoulders 221 of dispensing tip 220.

Figure 13:
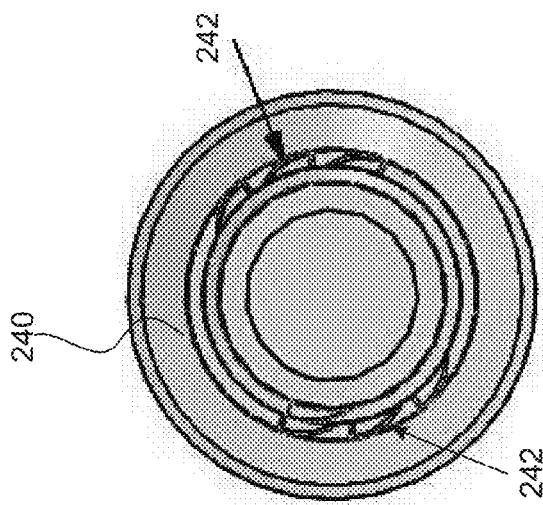
FIG. 13 is a top view of the bottle shown in FIG. 12.
Figure 12:
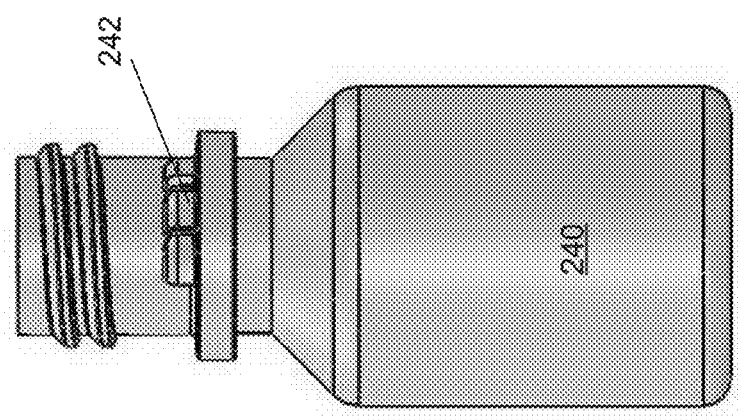
FIG. 12 is a dispensing bottle usable with the system of FIG. 7.
Figure 11:
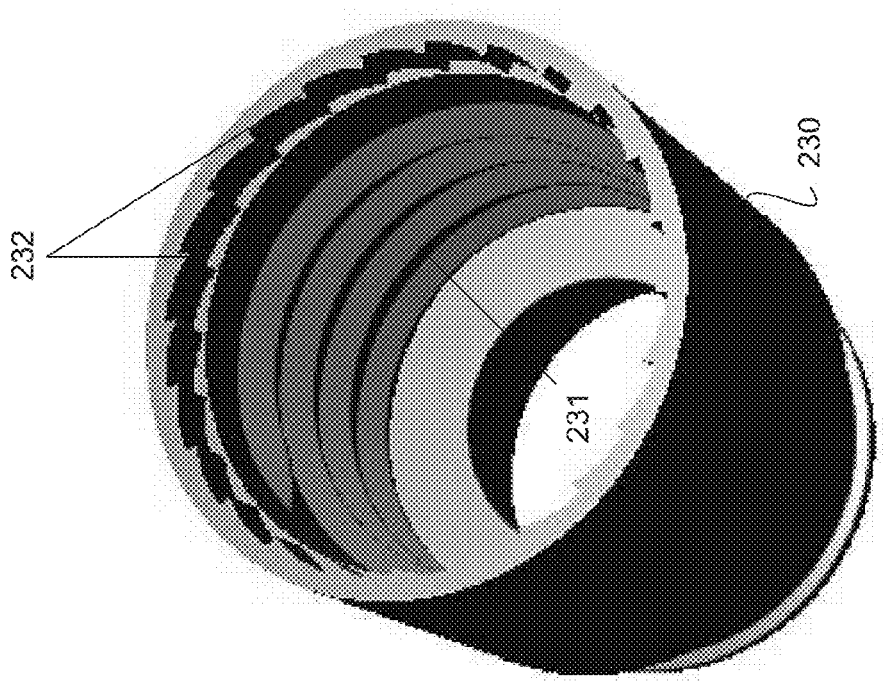
FIG. 11 is a bottom perspective view of a base according to the system of FIG. 7.

FIG. 11 is a bottom perspective view of a base according to the system of FIG. 7, FIG. 12 is a dispenser bottle usable with the system of FIG. 7, and FIG. 13 is a top view of the bottle shown in FIG. 12. Referring to FIGS. 11-13, an anti-back off feature has been added to both the dispenser bottle 240 and base 230. The base 230 is formed with internal threads 231 and serrated teeth 232 at its bottom skirt. Upon full seating of the base 230 to the bottle 240, the downward force of application will push the bottom skirt of the base 230 over formed teeth 242 in the bottle 240, providing a secure method of application where tampering to remove the base 230 would be evident and would eliminate accidental removal.

Figure 14:
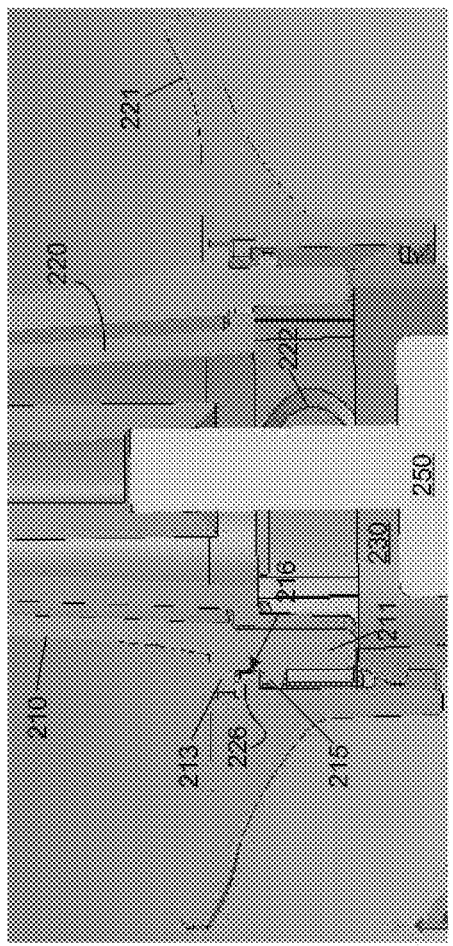
FIG. 14 is a portion of a sectional view taken of the system to show a locked condition.
Figure 16:
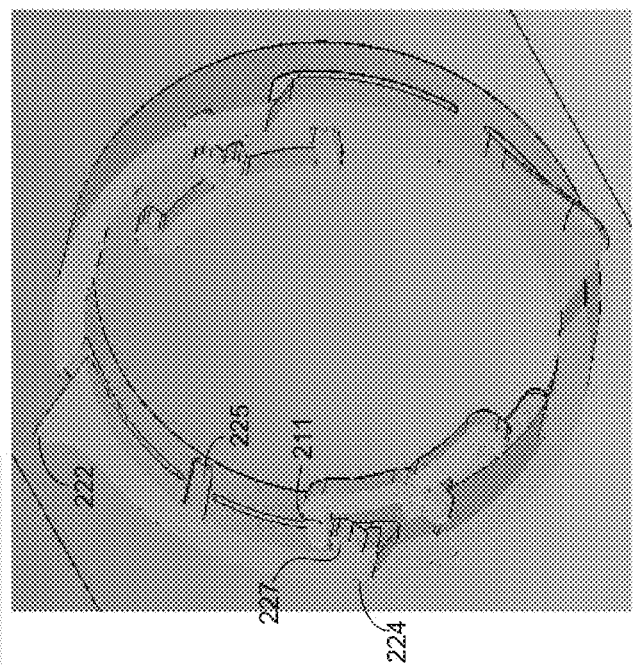
FIG. 16 is a portion of a cross-cut of the cap and dispensing tip in the xz-plane to show positions of the legs and buttons in a locked position.
Figure 15:
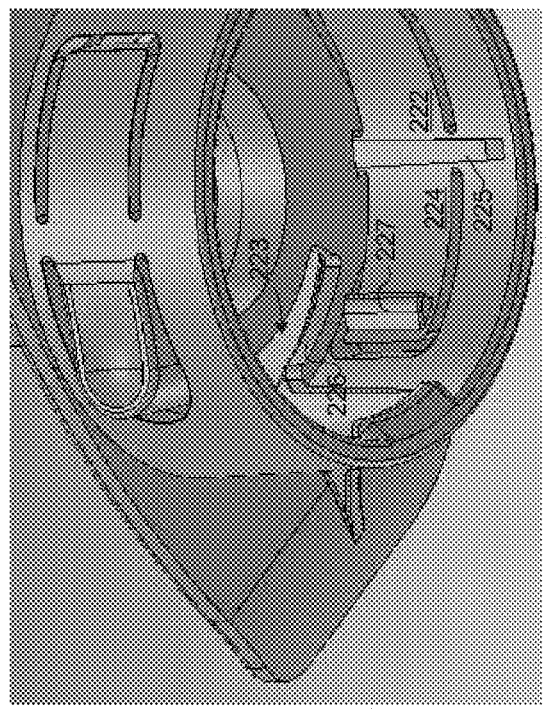
FIG. 15 is a partial bottom perspective view of the dispensing tip.

FIG. 14 is a portion of a sectional view taken of the system to shown a locked condition; FIG. 15 is a partial bottom perspective view of the dispensing tip, and FIG. 16 is a portion of a cross-cut of the cap and dispensing tip in the xz-plane to show positions of the legs and buttons in a locked position. Referring to FIG. 16, once the cap 210 is placed on the dispensing tip 220, the legs 211 travel through the slots 223 and ride over the ramps 227 to lock into place, as best shown in FIG. 16. In this locked condition, collar 226 of the dispensing tip 220 is retained between the rim 213 of cap 210 and the rib 215, as best seen in FIG. 14. The leg 211 extends all the way down to the base 230, locking out movement of the shoulders 221 and hence sprayer pump unit 250.

To unlock for operation, the user depresses both buttons 222 inward. This causes the ramps 227 to cant outward by way of the cam action of hinges 225. This allows legs 211 free travel. The user then rotates the cap 210 30 degrees after having depressed both buttons 222 to release the cap 210 from the dispensing tip 220. With the cap removed, actuation is now possible via shoulders 221.

Although the embodiment shown in FIGS. 7-16 describes a cap 210 having two legs that is twist to lock, in which the cap locks out actuation of a nasal pump sprayer, the exact same embodiment can be accomplished with a cap 210 having a single button actuating a single leg 211. The functions of locking and unlocking operations described above with a single button, having essentially the same construction and functionality as button 222 on dispensing tip 220, and a single leg having the same construction as leg 211, would accomplish the same goal of locking out shoulder 221 of the dispensing tip 220, as the leg 211 would extend all the way to base 230. The other side would by legless but have a dummy button for manufacturing purposes.

Figure 18:
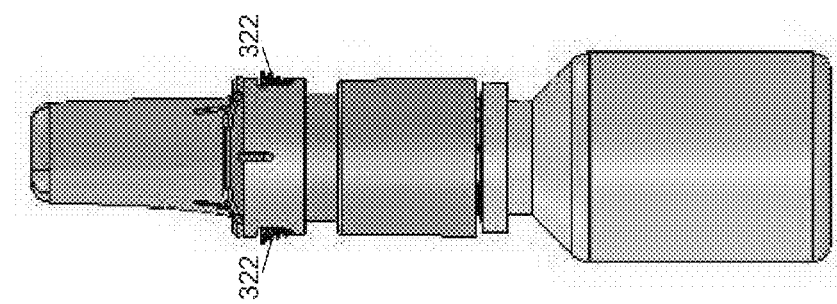
FIG. 18 is a side view of the system of FIG. 17.
Figure 17:
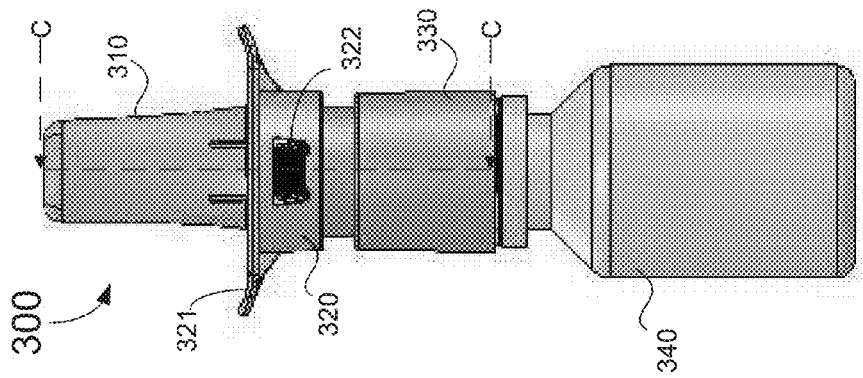
FIG. 17 is a front view of a child-resistant closure system for a pump sprayer according to another example embodiment.

FIG. 17 is a front view of a child-resistant closure system for a pump sprayer according to another example embodiment, and FIG. 18 is a side view of the system of FIG. 17. Referring to FIGS. 17 and 18, the child-resistant closure (CRC) system 300 includes a cap 310, a dispensing tip 320 and a base 330. Each of the cap 310, dispensing tip 320 and base 330 may be injection molded or extruded or otherwise formed of a suitable plastic material, as is known. The cap 310 is 3-sided to minimize rolling and avoid losing the cap 310. The dispensing tip 320 includes a pair of buttons 322 to allow cap 310 removal to permit sprayer pump unit 350 (not shown) actuation via the shoulders 321. The base 330 has interior grooves or threads for coupling it to a threaded member on dispenser bottle 340 which holds the medicinal fluid therein. The base 330 and dispensing tip 320 also enclose part of the sprayer pump unit 350 (not shown) which partly extends into the dispenser bottle 340 interior.

The base 330 and dispenser bottle 340 have serrations similar to that shown in FIGS. 11-13. In other words, an anti-back off feature is included. The base 330 is formed with internal threads and serrated teeth at its bottom skirt. Upon full seating of the base 330 to the bottle 340, the downward force of application pushes the bottom skirt of the base 330 over formed teeth in the bottle 340, providing a secure method of application where tampering to remove the base 330 would be evident and would eliminate accidental removal.

Figure 19:
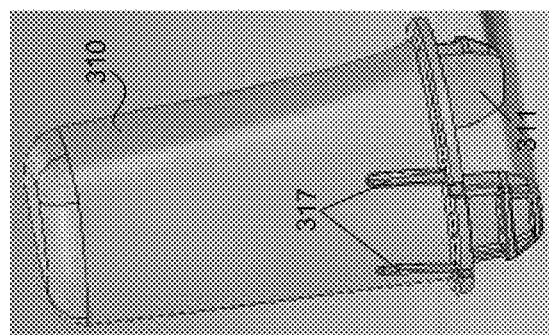
FIG. 19 is a perspective view of a cap according to the system of FIG. 17.
Figure 20:
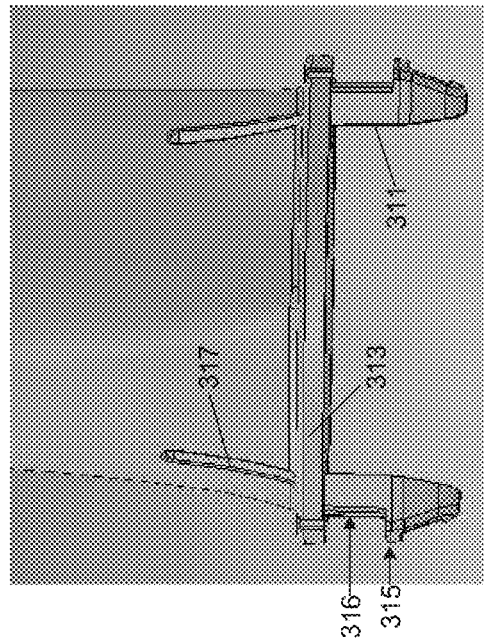
FIG. 20 is a close-up view of the lower portion of the cap shown in FIG. 19.

FIG. 19 is a perspective view of a cap according to the system of FIG. 17, and FIG. 20 is a close-up view of the lower portion of the cap shown in FIG. 19. Referring to FIGS. 19 and 20, the cap 310 has slits or reliefs 317 formed therein to provide flexibility. Additionally, each leg 311 is tapered and includes a rib 315 and the rim 313 of the cap 311 sandwiching an undercut 316.

FIG. 21 is a close-up view of a lower portion of a dispensing tip according to the system of FIG. 17. Each button 322 has a cutout on three sides, enhancing flexibility inward. The buttons 322 are located on a collar 326 of the dispensing tip 320, and the dispensing tip 320 includes support ribs 328 to provide strength for the shoulders 321. As will be seen hereafter, depression of both buttons 322 simultaneously actuates the two legs 311 inward, allowing cap 310 removal.

FIG. 22 is sectional view C-C taken from FIG. 17. Referring to FIG. 22, with the cap 310 in place, actuation is locked out, with the legs 311 contacting the base 330. The cap 310 is retained in slots 323 biased against undercuts 316 between ribs 315 and rim 313. When engaging, the legs 311 will temporarily deflect inwards until the undercuts 316 pass cutouts on the dispensing tip 320 where they will snap back to vertical, with ribs 315 and rim 313 engaging. As noted, the legs 311 extend to the top of the base 330 and allow for the sprayer pump unit 350 (by way of shoulders 321) to be locked out while the cap 310 is in place. FIG. 25 also shows the internal threads 331 and serrations 332 of the base 330 which provide the anti-back off feature and hence a mechanical bond with the top serrations (teeth) on dispenser bottle 340.

To release the cap 310, the buttons 322 on the collar 326 of dispensing tip 320 are to be pressed simultaneously, causing the legs 311 to once again deflect inwards away and off of base 330, deflecting its corresponding ribs 315 as well, and the cap 310 can be drawn up through slots 323 and off of the dispensing tip 320. With cap 310 removed, downward movement of the shoulders 321 to actuate the sprayer pump unit 350 within dispensing tip 320 and base 330 is possible.

FIG. 23 is a front view of a child-resistant closure system for a pump sprayer according to another example embodiment. The child-resistant closure (CRC) system 400 includes a cap 410, a dispensing tip 420 and a base 430. Each of the cap 410, dispensing tip 420 and base 430 may be injection molded or extruded or otherwise formed of a suitable plastic material, as is known. The cap 410 is 3-sided to minimize rolling and avoid losing the cap 410. The cap 410 includes a pair of buttons 412 to allow cap 410 removal to permit sprayer pump unit 450 (not shown) actuation via the shoulders 421. The base 430 has interior grooves or threads for coupling it to a threaded member on dispenser bottle 440 which holds the medicinal fluid therein. The base 430 and dispensing tip 420 also enclose the sprayer pump unit 450 (not shown) which partly extends into the dispenser bottle 440 interior.

The base 430 and dispenser bottle 440 have serrations similar to that shown in FIGS. 11-13; in other words, an anti-back off feature is included. The base 430 is formed with internal threads and serrated teeth at its bottom skirt. Upon full seating of the base 430 to the bottle 440, the downward force of application pushes the bottom skirt of the base 430 over formed teeth in the bottle 440, providing a secure method of application where tampering to remove the base 430 would be evident and would eliminate accidental removal.

FIG. 24 is a front view of a cap according to the system of FIG. 23. The cap 410 has slits or reliefs 417 formed on either side of button 412 to provide flexibility. Additionally, each leg 411 is tapered and includes a rib 415 and the rim 413 of the cap 411 sandwiching an undercut 416.

FIG. 25 is sectional view C-C taken from FIG. 23. Referring to FIG. 25, with the cap 410 in place, actuation is locked out, with the legs 411 contacting the base 430. The cap 410 is retained in slots 423 biased against undercuts 416 between ribs 415 and rim 413. When engaging, the legs 411 will temporarily deflect inwards until the undercuts 416 pass cutouts on the dispensing tip 420 where they will snap back to vertical, with ribs 415 and rim 413 engaging. As noted, the legs 411 extend to the top of the base 430 and allow for the sprayer pump unit 450 (by way of shoulders 421) to be locked out while the cap 410 is in place. FIG. 25 also shows the internal threads 431 and serrations 432 of the base 430 which provide the anti-back off feature and hence a mechanical bond with the top serrations (teeth) on dispenser bottle 440.

To release the cap 410, the buttons 412 on the cap 410 are to be pressed simultaneously, causing the legs 411 to once again deflect inwards away and off of base 430, deflecting its corresponding ribs 415 as well, and the cap 410 can be drawn up through slots 423 and off of the dispensing tip 420. With cap 410 removed, downward movement of the shoulders 421 to actuate the sprayer pump unit 450 is possible.

FIG. 26 is a front view of a child-resistant closure system for a pump sprayer according to another example embodiment. The child-resistant closure (CRC) system 500 includes a cap 510, a dispensing tip 520 and a base 530. Each of the cap 510, dispensing tip 520 and base 530 may be injection molded or extruded or otherwise formed of a suitable plastic material, as is known. The cap 510 is 3-sided to minimize rolling and avoid losing the cap 510. The dispensing tip 520 includes a pair of buttons 522 on a surface thereof to allow cap 510 removal to permit sprayer pump unit 550 (not shown) actuation via the shoulders 521. The base 530 has interior grooves or threads for coupling it to a threaded member on dispenser bottle 540 which holds the medicinal fluid therein. The base 530 and dispensing tip 520 also partially enclose the sprayer pump unit 550 (not shown) which partly extends into the dispenser bottle 540 interior.

The base 530 and dispenser bottle 540 have serrations similar to that shown in FIGS. 11-13; in other words, an anti-back off feature is included. The base 530 is formed with internal threads and serrated teeth at its bottom skirt. Upon full seating of the base 530 to the bottle 540, the downward force of application pushes the bottom skirt of the base 530 over formed teeth in the bottle 540, providing a secure method of application where tampering to remove the base 530 would be evident and would eliminate accidental removal.

FIG. 27 is a perspective view of a cap according to the system of FIG. 26. The cap 310 includes a pair of spaced legs 511. Each leg 511 includes a rib 515 and the rim 513 of the cap 511 sandwiching an undercut 516.

FIG. 28 is a front perspective view of a dispensing tip according to the system of FIG. 26. The dispensing tip 420 includes a collar on which is disposed the buttons 522. The shoulders include a pair of slots 523 through which the cap 510 is inserted. The rear side of each button 522 has a ramp 527 that is designed as a stop to lock a leg 511 in place in a locked condition.

Figure 30:
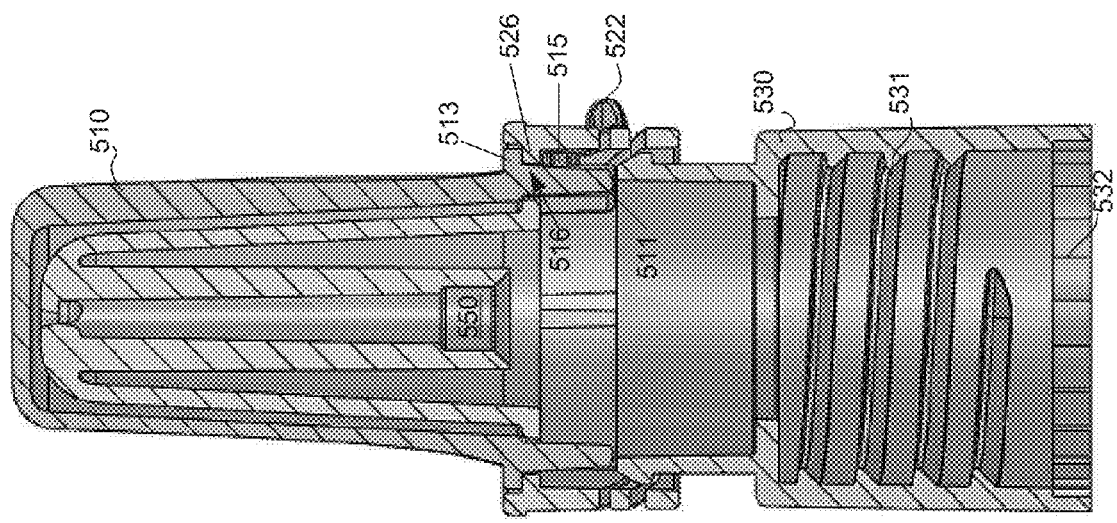
FIG. 30 is sectional view C-C taken from FIG. 26.
Figure 29:
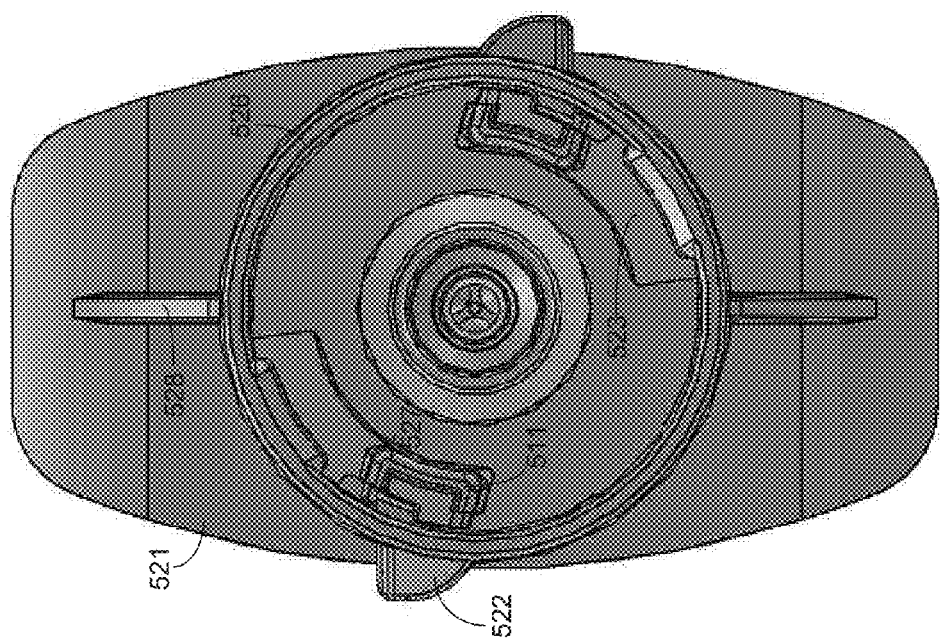
FIG. 29 is a top view of the dispensing tip of FIG. 28.

FIG. 29 is a top view of the dispensing tip of FIG. 28, and FIG. 30 is a sectional view C-C taken from FIG. 26. Referring to FIGS. 29 and 30, with the cap 510 inserted through the slots 523 in place, the legs 511 contacting base 530 and the ribs 515 and rim 513 sandwiching internal elements of collar 526 of the dispensing tip 520, operation of the shoulders 521 is locked out; actuation of sprayer pump unit 550 is not possible. Specifically, the cap 510 is retained by the two legs 511, with vertical undercuts that engage the two ramps 527 that extend from the back side of the buttons 522 on the collar 526. When engaging, the cap 510 is placed and turned in a clockwise motion; this will press the legs 511 against the ramps 527. This in turn forces the ramps 527 to deflect downwards until the undercuts 516 on the cap 510 pass. Once clear, the ramps 527 snap into position behind the undercuts 516 on the legs 511 and lock the cap 510 in place.

As noted, the legs 511 extend to the top of the base 530 and allow for the sprayer pump unit 550 (by way of shoulders 521) to be locked out while the cap 510 is in place. FIG. 29 also shows the internal threads 531 and serrations 532 of the base 530 which provide the anti-back off feature and hence a mechanical bond with the top serrations (teeth) on dispenser bottle 540.

To release the cap 510, the buttons 522 on the collar 526 of dispensing tip 520 must be pressed simultaneously in a vertical downward motion, causing the legs 511 to once again deflect downwards and the cap 511 can be turned in a counter-clockwise motion, drawn up through slots 523, and off of the dispensing tip 520. With cap 510 removed, downward movement of the shoulders 521 to actuate the sprayer pump unit 550 within dispensing tip 520 and base 530 is possible.

Figure 33:
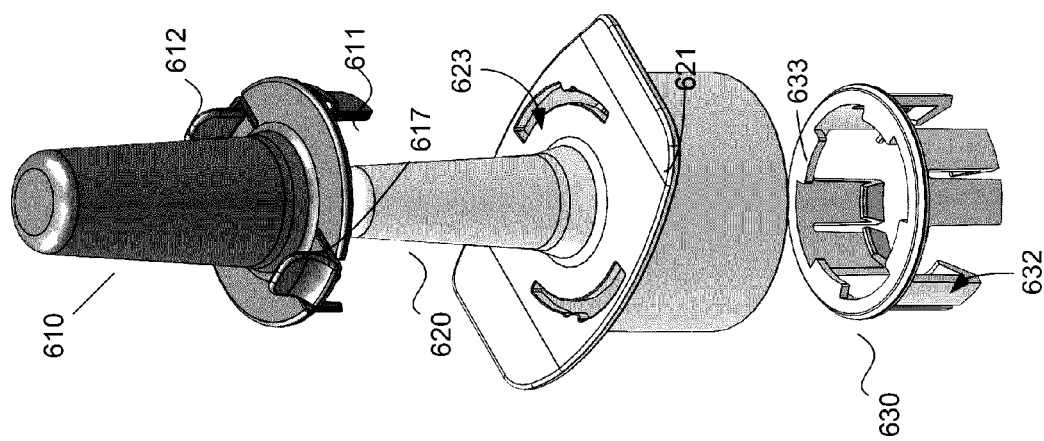
FIG. 33 is an exploded view of selected components of the system of FIG. 31.
Figure 32:
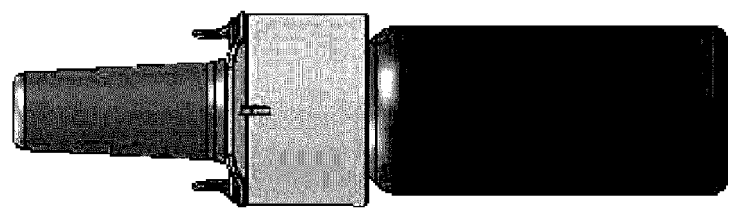
FIG. 32 is a side view of the system of FIG. 31.
Figure 31:
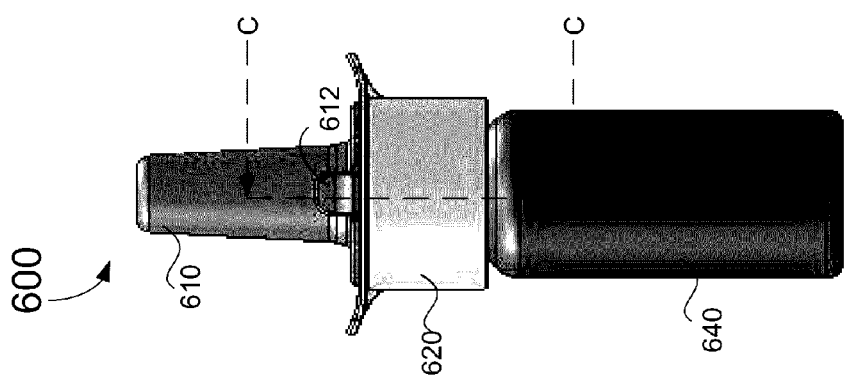
FIG. 31 is a front view of a child-resistant closure system for a pump sprayer according to another example embodiment.

FIG. 31 is a front view of a child-resistant closure system for a pump sprayer according to another example embodiment; FIG. 32 is a side view of the system of FIG. 31; and FIG. 33 is an exploded view of selected components of the system of FIG. 31. Referring to FIGS. 31-33, the child-resistant closure (CRC) system 600 includes a cap 610, a dispensing tip 620 and a retainer collar 630. Each of the cap 610 and dispensing tip 620 may be injection molded or extruded or otherwise formed of a suitable plastic material, as is known; the retainer collar 630 may be formed of a metal or plastic material. The cap 610 includes a pair of upstanding levers 612 to allow cap 610 removal to permit sprayer pump unit 650 (not shown) actuation via the shoulders 621. Each lever 612 has a slit or relief 617 on either side thereof to promote flexibility. Unlike previous embodiments which are threaded, the dispenser bottle 640 here is a ferrule type dispenser bottle. As such, the retainer collar 630 is provided with clamp elements 632 and top projections 633 to provide a positive mechanical bond to the upper ferrule portion of the bottle 640 which holds the medicinal fluid therein. Once installed, this cannot be broken by a 5-year old or younger child. The dispensing tip 620 partly encloses the sprayer pump unit 850 (not shown) which also partly extends into and is enclosed by the dispenser bottle 840 interior.

The legs 611 of the cap 610 are designed to be inserted into slots 623 present in the shoulders 621 of the dispensing tip 620. The retainer collar 630 is secured within the dispensing tip 620 interior atop the upper ferrule portion of bottle 640.

Figure 34:
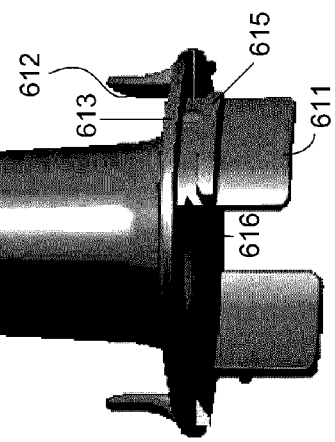
FIG. 34 is a perspective view of a cap according to the system of FIG. 31.
Figure 35:
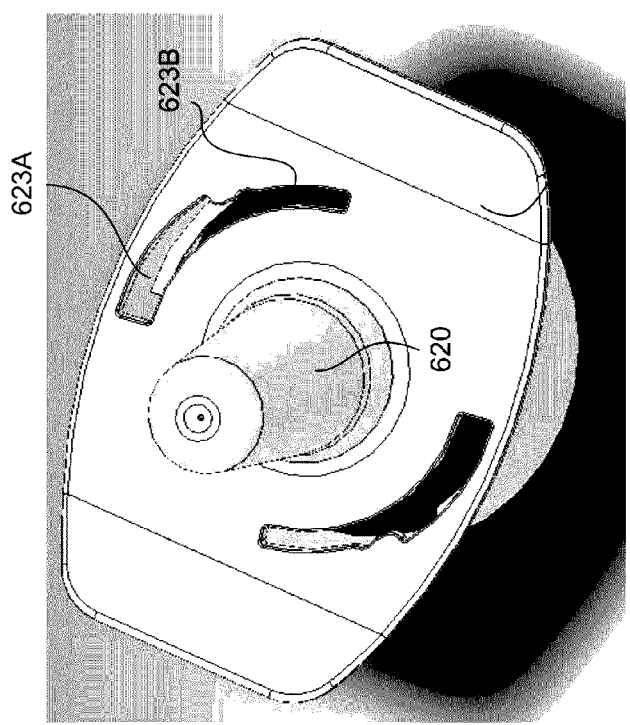
FIG. 35 is a top view of the dispensing tip of FIG. 33.

FIG. 34 is a perspective view of a cap according to the system of FIG. 31, and FIG. 35 is a top view of the dispensing tip of FIG. 33. Referring to FIGS. 34 and 35, the cap 610 includes a pair up spaced upstanding levers 612, and a corresponding deflection tab 614 beneath each lever 612. As will be seen, and referring to FIG. 35, upon rotation of the cap 610 clockwise into a locked position, each tab 614 engages with the underside of a shoulder 621 in the narrower slot portion 623B to lock out the cap 610 and prevent it from disengagement. The cap leg 611 includes a rib 615 that sandwiches an undercut 616 between the rib 613 of the cap 610. This undercut 616 also temporarily contacts a portion of the shoulder 621 of dispensing tip 620 through leg 611 rotation along slot 623B to its final locked location, before rotation is stopped by tab 614 in slot 623B, causing the bottom of leg 611 to bear on base 630 in the locked condition. The locked condition is achieved via depressing the levers 612 inward simultaneously, and turning the cap 610 clockwise with legs inserted in slots, rotating from slot portion 623A to portion 623B.

Figure 36:
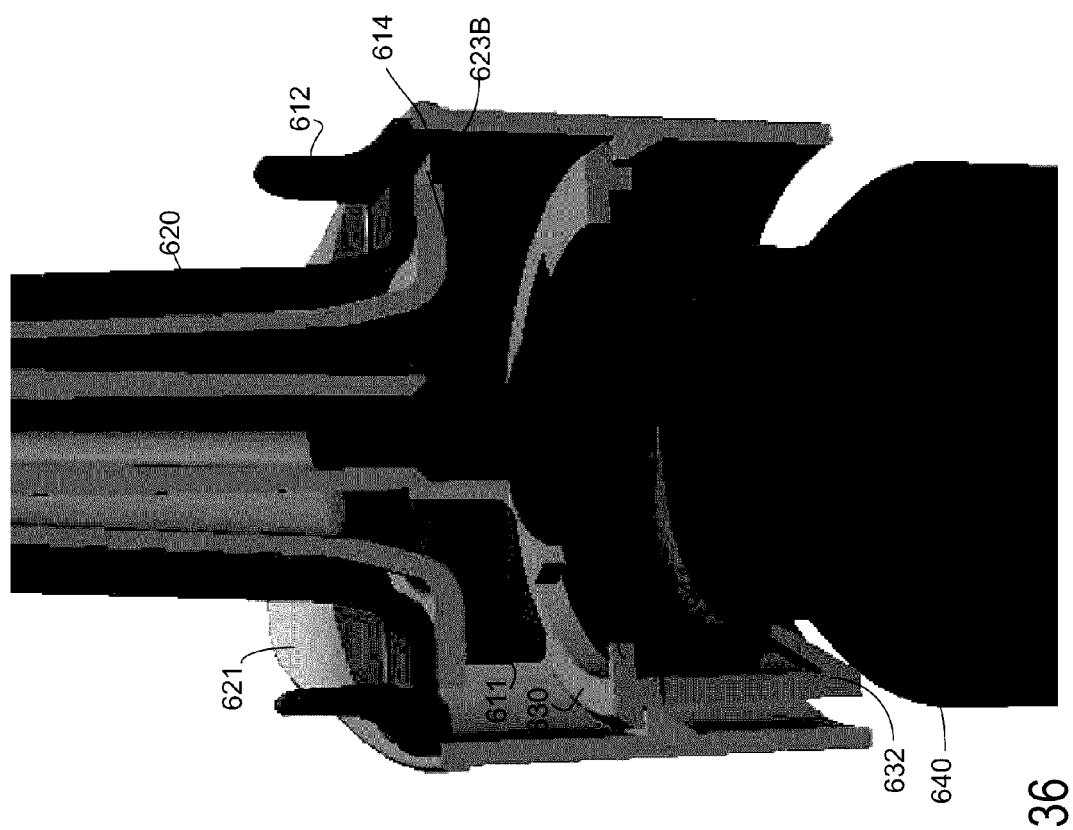
FIG. 36 is sectional view C-C taken from FIG. 31.

FIG. 36 is sectional view C-C taken from FIG. 31. With the cap 610 inserted through the slots 623A and rotated clockwise to slots 623B in place, the legs 611 contacting base 630, operation of the shoulders 621 is locked out; actuation of sprayer pump unit 650 is not possible. Specifically, the cap 610 is retained by the two legs 611, with undercuts 616 that engage with the underside of the slots 623B on the shoulders 621 of the dispensing tip 620, and the two tabs 614 that extend from the levers 612 on the cap 610. When engaging, the legs 611 will pass the slots 623B and engage with the dispensing tip 620 once turned clockwise. At the end of the turning motion, the tabs 614 deflect downward and engage with the shoulder 621 portion at slot 623B to lock out the cap 610 and keep it from disengagement.

As noted, the legs 611 extend to the top of the base 630 and allow for the sprayer pump unit 650 (by way of shoulders 621) to be locked out while the cap 610 is locked in place.

FIG. 36 also shows the clamp elements 632 and top projections 633 which provide a positive mechanical bond to the upper ferrule portion 641 of the dispenser bottle 640. Specifically, the clamp elements 632 crimp to the underside of the lip of the ferrule portion 641 of the dispenser bottle 640, providing an upward engagement pressure, with the projections 633 providing a positive engagement pressure on the ferrule portion 641 top surface, solidifying the mechanical bond.

To release the cap 610, the levers 612 must be pressed inward simultaneously, causing the tabs 614 to deflect upwards. The cap 611 is then turned in a counter-clockwise motion, drawn up through wider slot portions 623A, and off of the dispensing tip 620. With cap 610 removed, downward movement of the shoulders 621 to actuate the sprayer pump unit 650 is possible.

FIG. 37 is a front view of a child-resistant closure system for a pump sprayer according to another example embodiment, and FIG. 38 is an exploded view of selected components of the system of FIG. 37. Referring to FIGS. 37 and 38, the child-resistant closure (CRC) system 700 includes a cap 710, a dispensing tip 720 and a retainer collar 730. Each of the cap 710 and dispensing tip 720 may be injection molded or extruded or otherwise formed of a suitable plastic material, as is known; the retainer collar 730 may be formed of a metal or plastic material. The dispensing tip 720 includes a pair of spaced buttons 722 on opposite sides of a collar 726 thereof beneath shoulders 721 of the dispensing tip 720 to allow cap 710 removal and permit sprayer pump unit 750 (not shown) actuation via the shoulders 721. Unlike previous embodiments which are threaded, the dispenser bottle 740 here is a ferrule type dispenser bottle. As such, the retainer collar 730 is provided with clamp elements 732 and top projections 733 to provide a positive mechanical bond to the upper ferrule portion of the bottle 740 which holds the medicinal fluid therein. Once installed, this cannot be broken by a 5-year old or younger child. The dispensing tip 720 partly encloses the sprayer pump unit 750 (not shown) which also partly extends into and is enclosed by the dispenser bottle 740 interior.

The legs 711 of the cap 710 are designed to be inserted into slots 723 present in the shoulders 721 of the dispensing tip 720. The retainer collar 730 is secured within the dispensing tip 720 interior atop the upper ferrule portion of bottle 740.

FIG. 39 is a perspective view of a cap according to the system of FIG. 37, and FIG. 40 is a front rotated view of the dispensing tip of FIG. 38. Referring to FIGS. 39 and 40, cap 710 has a pair of legs 711 extending downward on either side. Each leg 711 has a rib 715 separated from the rim 713 of the cap 711 by an undercut 716. Dispensing tip 720 includes a pair of shoulders 721 that are used to depress the sprayer pump unit 750 within (not shown) under finger pressure, as is known. On either side of the collar 726 of dispensing tip 720 is provided a pair of buttons 722 with reliefs 724 separated by a hinge 725 that acts as a cam when the button 722 is actuated by the user. A ramp 727 is positioned on the back side of each relief 724; this ramp 727 interfaces with each leg 711 once the legs 211 are inserted through slots 723 in the shoulders 721 of dispensing tip 720.

Figure 42:
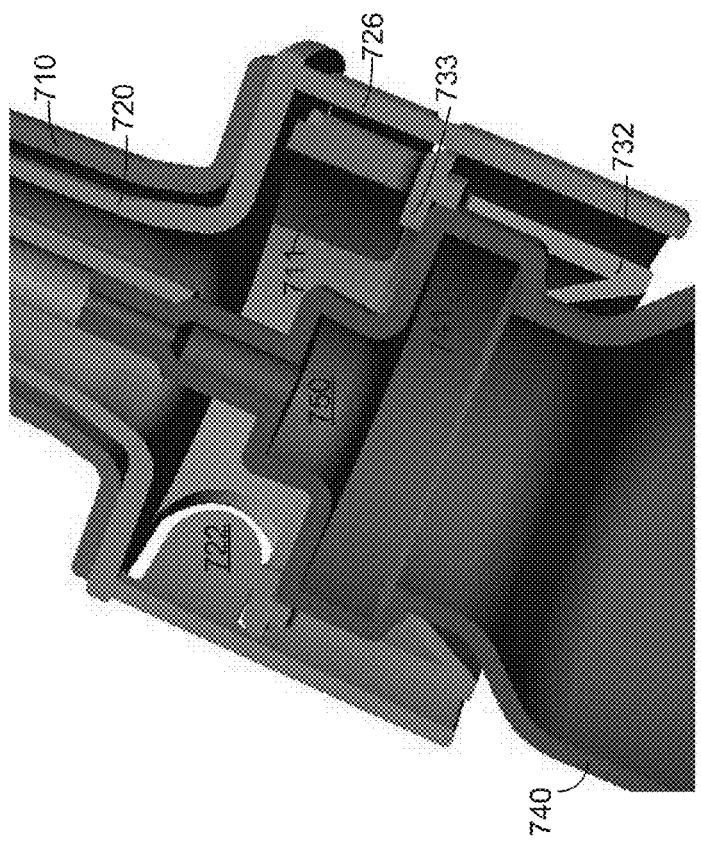
FIG. 42 is a portion of a sectional view of the system in the yz-plane to illustrate a locked condition.
Figure 41:
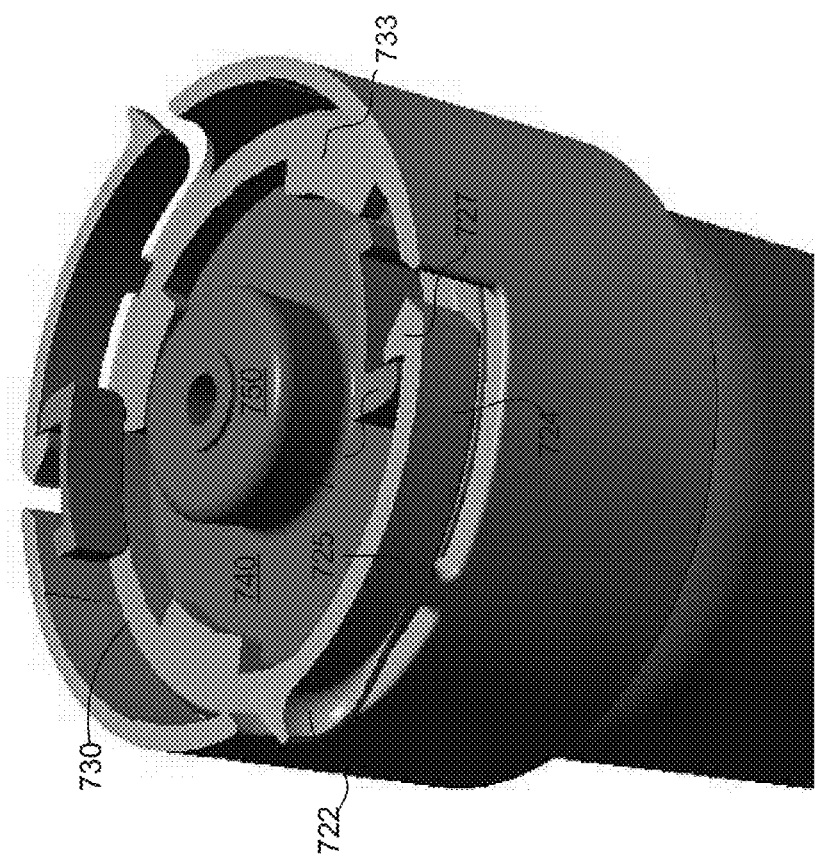
FIG. 41 is a portion of a sectional view of the dispensing tip and legs in the xz-plane with selected components removed to illustrate a locked condition.

FIG. 41 is a portion of a sectional view of the dispensing tip and legs in the xz-plane with selected components removed to illustrate a locked condition, and FIG. 42 is a portion of a sectional view of the system in the yz-plane to illustrate a locked condition. Referring to FIGS. 41 and 42, once the cap 710 is placed on the dispensing tip 720, the legs 711 travel through the slots 723 and ride over the ramps 727 to lock into place, as best shown in FIG. 41. In this locked condition, collar 726 of the dispensing tip 720 is retained between the rim 713 of cap 710 and the rib 715. As shown in FIG. 42, the leg 711 extends all the way down to the retainer collar 730, locking out movement of the shoulders 721 and hence sprayer pump unit 750.

To unlock for operation, the user depresses both buttons 722 inward. Referring to FIG. 41, this causes the ramps 727 to cant outward by way of the cam action of hinges 725. This allows legs 711 free travel. The user then rotates the cap 710 30 degrees (into the wider part of slot 723, see FIG. 38) after having depressed both buttons 722 to release the cap 710 from the dispensing tip 720. With the cap 710 removed, actuation of sprayer pump unit 750 is now possible via shoulders 721.

FIG. 42 also shows the clamp elements 732 and top projections 733 which provide a positive mechanical bond to the upper ferrule portion 741 of the dispenser bottle 740. Specifically, the clamp elements 732 crimp to the underside of the lip of the ferrule portion 741 of the dispenser bottle 740, providing an upward engagement pressure, with the projections 733 providing a positive engagement pressure on the ferrule portion 741 top surface, solidifying the mechanical bond.

FIG. 43 is a front view of a child-resistant closure system for a pump sprayer according to another example embodiment, FIG. 44 is an exploded view of selected components of the system of FIG. 43, and FIG. 45 is a perspective view of a cap according to the system of FIG. 43. Referring to FIGS. 43-45, the child-resistant closure (CRC) system 800 includes a cap 810, a dispensing tip 820 and a retainer collar 830. Each of the cap 810 and dispensing tip 820 may be injection molded or extruded or otherwise formed of a suitable plastic material, as is known; the retainer collar 830 may be formed of a metal or plastic material. The dispensing tip 820 includes a pair of spaced buttons 822 on opposite sides thereof beneath shoulders 821 of the dispensing tip 820 to allow cap 820 removal and permit sprayer pump unit 850 (not shown) actuation via the shoulders 821. Each button 822 has a cutout on three sides, enhancing flexibility inward. The buttons 822 are located on a collar 826 of the dispensing tip 320. As will be seen hereafter, depression of both buttons 822 simultaneously actuates the two legs 811 inward, allowing cap 810 removal.

As dispenser bottle 840 here is a ferrule type dispenser bottle, the retainer collar 830 is provided with clamp elements 832 and top projections 833 to provide a positive mechanical bond to the upper ferrule portion of the bottle 840 which holds the medicinal fluid therein. The retainer collar 830 is secured within the dispensing tip 820 interior atop the upper ferrule portion of bottle 840. The dispensing tip 820 partly encloses the sprayer pump unit 850 (not shown) which also partly extends into and is enclosed by the dispenser bottle 840 interior.

The legs 811 of the cap 810 are designed to be inserted into slots 823 formed through the shoulders 821 of the dispensing tip 820. The cap 810 has slits or reliefs 817 formed therein to provide flexibility. Additionally, each leg 811 is tapered and includes a rib or thickened portion 815 and the rim 813 of the cap 810 sandwiching an undercut 816.

FIG. 46 is sectional view C-C taken from FIG. 43. Referring to FIG. 43, with the cap 810 in place, actuation is locked out, with the legs 811 contacting the retainer collar 830. The cap 810 is retained in slots 823 with a section of shoulder 821 biased against undercuts 816 and engaged between ribs 815 and rim 813. When engaging, the legs 811 will temporarily deflect inwards until the undercuts 816 pass cutouts on the shoulder 821 of the dispensing tip 820, where they will snap back to vertical, with ribs 815 and rim 813 engaging. As noted, the legs 811 extend to the top of the retainer collar 830 and allow for the sprayer pump unit 850 (by way of shoulders 821) to be locked out while the cap 810 is in place.

To release the cap 310, the buttons 822 on the collar 826 of dispensing tip 820 are to be pressed simultaneously, causing the legs 811 to once again deflect inwards away and off of retainer collar 830, deflecting its corresponding ribs 815 as well, and the cap 810 can be drawn up through slots 823 and off of the dispensing tip 820. With cap 810 removed, downward movement of the shoulders 821 to actuate the sprayer pump unit 850 is possible.

FIG. 46 also shows the clamp elements 832 and top projections 833 which provide a positive mechanical bond to the upper ferrule portion 841 of the dispenser bottle 840. Specifically, the clamp elements 832 crimp to the underside of the lip of the ferrule portion 841 of the dispenser bottle 840, providing an upward engagement pressure, with the projections 833 providing a positive engagement pressure on the ferrule portion 841 top surface, solidifying the mechanical bond.

FIG. 47 is a front view of a child-resistant closure system for a pump sprayer according to another example embodiment, FIG. 48 is an exploded view of selected components of the system of FIG. 47, and FIG. 49 is a perspective view of a cap according to the system of FIG. 47. Referring to FIGS. 47-49, the child-resistant closure (CRC) system 900 includes a cap 910, a dispensing tip 920 and a retainer collar 930. Each of the cap 910 and dispensing tip 920 may be injection molded or extruded or otherwise formed of a suitable plastic material, as is known; the retainer collar 930 may be formed of a metal or plastic material. The cap 910 includes a pair of spaced buttons 912 on opposite sides thereof to allow cap 910 removal and permit sprayer pump unit 950 (not shown) actuation via the shoulders 921. Each button 922 has a slit or relief 917 on either side thereof, enhancing flexibility inward. As will be seen hereafter, depression of both buttons 912 simultaneously actuates the two legs 911 inward, allowing cap 910 removal.

As dispenser bottle 940 here is a ferrule type dispenser bottle, the retainer collar 930 is provided with clamp elements 932 and top projections 933 to provide a positive mechanical bond to the upper ferrule portion of the bottle 940 which holds the medicinal fluid therein. The retainer collar 930 is secured within the dispensing tip 920 interior atop the upper ferrule portion of bottle 940. The dispensing tip 920 partly encloses the sprayer pump unit 950 (not shown) which also partly extends into and is enclosed by the dispenser bottle 940 interior.

The legs 911 of the cap 910 are designed to be inserted into slots 923 formed through the shoulders 921 of the dispensing tip 920. Each leg 911 is tapered and includes a rib or thickened portion 915 and the rim 913 of the cap 910 sandwiching an undercut 916.

FIG. 50 is sectional view C-C taken from FIG. 47. The cap 910 is retained in slots 923 with a section of shoulder 921 biased against undercuts 916 and engaged between ribs 915 and rim 913. When engaging, the legs 911 will temporarily deflect inwards until the undercuts 916 pass cutouts on the dispensing tip 920 where they will snap back to vertical, with ribs 915 and rim 913 engaging. As noted, the legs 911 extend to the top of the retainer collar 930 and allow for the sprayer pump unit 950 (by way of shoulders 921) to be locked out while the cap 910 is in place.

To release the cap 910, the buttons 912 on the cap 910 are to be pressed simultaneously, causing the legs 911 to once again deflect inwards away and off of retainer collar 930, deflecting its corresponding ribs 915 as well, and the cap 910 can be drawn up through slots 923 and off of the dispensing tip 920. With cap 910 removed, downward movement of the shoulders 921 to actuate the sprayer pump unit 950 within dispensing tip 920 is possible.

FIG. 50 also shows the clamp elements 932 and top projections 933 which provide a positive mechanical bond to the upper ferrule portion 941 of the dispenser bottle 940. Specifically, the clamp elements 932 crimp to the underside of the lip of the ferrule portion 941 of the dispenser bottle 940, providing an upward engagement pressure, with the projections 933 providing a positive engagement pressure on the ferrule portion 941 top surface, solidifying the mechanical bond.

FIG. 51 is a perspective view of a child-resistant closure system for a pump sprayer according to another example embodiment, FIG. 52 is a perspective view of a cap according to the system of FIG. 51, FIG. 53 is a top view of the dispensing tip according to the system of FIG. 51, and FIG. 54 is a bottom perspective view of a base according to the system of FIG. 51. Referring to FIGS. 51-54, the child-resistant closure (CRC) system 1000 includes a cap 1010, a dispensing tip 1020 and a base 1030. Each of the cap 1010, dispensing tip 1020 and base 1030 may be injection molded or extruded or otherwise formed of a suitable plastic material, as is known. Although a dispenser bottle is not shown in this embodiment, this system 1000 is configured for use with threaded nasal sprayer dispenser bottles, such as shown in FIGS. 1-30, although the example embodiments are not so limited to use with nasal sprayer dispensers.

The cap 1010 is 3-sided to minimize rolling and avoid losing the cap 1010. Cap 1010 includes a pair of spaced legs 1011, with each leg 1011 having an upper rib 1015 bounding a first undercut 1016 and a lower rib 1018 bounding a second undercut 1019. The dispensing tip 1020 includes a skirt 1021 which has slots 1023 formed there through. A user depresses the skirt 1021 to actuate the sprayer pump unit within (not shown). The base 1030 includes interior threaded grooves 1031, an aperture 1034 for receiving a nozzle of a sprayer pump unit (not shown) there through into the dispensing tip 1020 and an upper lip 1035 for engagement to the lower rib 1018 of the leg 1011 when in a locked condition.

Optionally, the base 1030 can have the configuration shown in FIG. 11. Specifically, the base 1030 can be configured with serrations (teeth) on its skirt, so as to form a mechanical bond with a dispenser bottle upon screwing the base down onto the threads of the dispenser bottle to seat the system 1000 on the bottle.

FIG. 55 is a portion of a cross-cut of the cap and dispensing tip in a bottom view to show positions of the legs in the slots in a locked position, and FIG. 56 is a portion of a sectional view of the system in the yz-plane to illustrate a locked condition. Referring to FIGS. 55 and 56, the legs 1011 of cap 1010 are inserted into the wider opening portions 1023A of the slots and rotated clockwise to seat in the smaller opening portions 1023B. This locks out operation of the skirt 1021 and hence the sprayer pump unit, as the legs 1011 extends all the way down to the lip 1035 of the base 1030, with the lip 1035 captured in the undercut 1019 and the lower rib 1018 capturing the underside of lip 1035 to lock the cap 1010 in place. A friction fit lock is provided between the leg 1011 and the dimensional tolerances in slot 1023B, locking the leg in place at its upper end as well. This friction is strong enough so it cannot be turned counterclockwise by a 5-year old, providing a lock for the dispenser. An adult however, can overcome the frictional hold to turn the cap counterclockwise and place the legs into the wider portions 1023A of the slot to withdrawal the legs 1011. This also releases the lower rib 1018 from the lip 1035 at base 1030.

Figure 58:
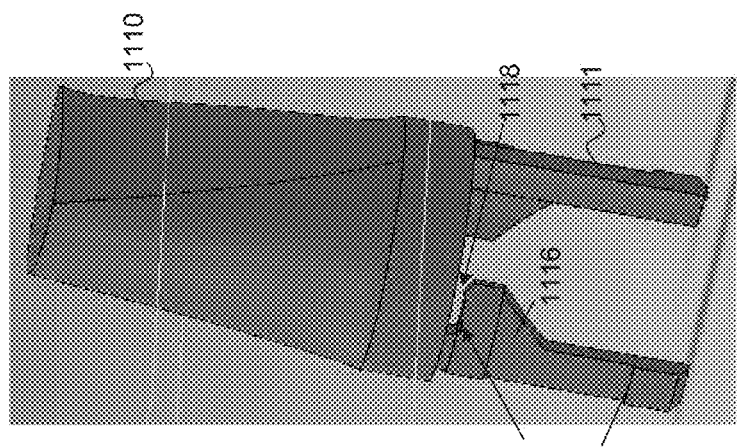
FIG. 58 is a perspective view of a cap according to the system of FIG. 57.
Figure 60:
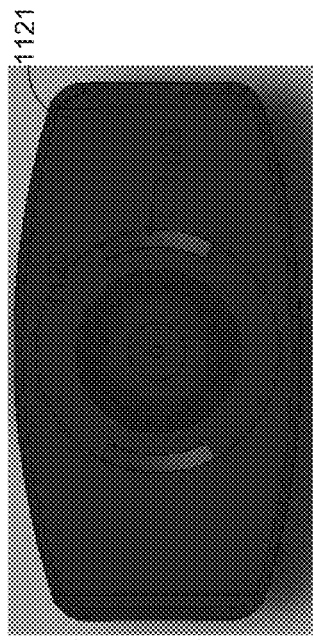
FIG. 60 is a top view of the dispensing according to the system of FIG. 57.
Figure 57:
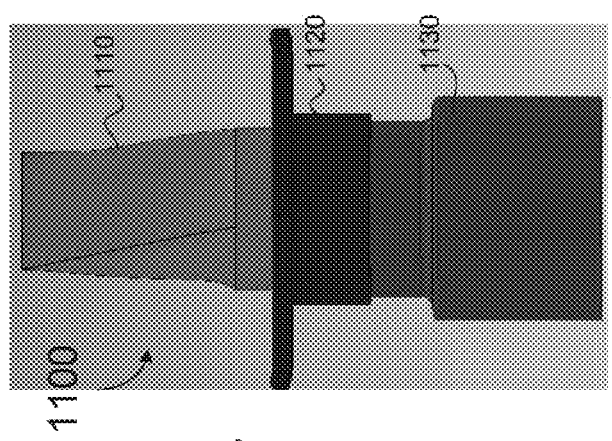
FIG. 57 is a front view of a child-resistant closure system for a pump sprayer according to another example embodiment.
Figure 59:
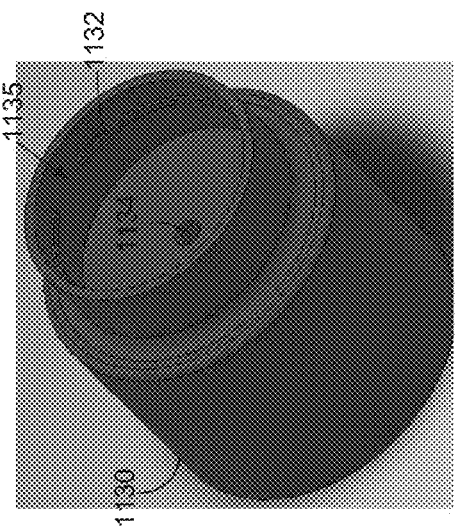
FIG. 59 is a top perspective view of a base according to the system of FIG. 57.

FIG. 57 is a front view of a child-resistant closure system for a pump sprayer according to another example embodiment, FIG. 58 is a perspective view of a cap according to the system of FIG. 57, FIG. 59 is a top perspective view of a base according to the system of FIG. 57, and FIG. 60 is a top view of the dispensing according to the system of FIG. 57. Referring to FIGS. 57-60, the child-resistant closure (CRC) system 1100 includes a cap 1110, a dispensing tip 1120 and a base 1130. Each of the cap 1110, dispensing tip 1120 and base 1130 may be injection molded or extruded or otherwise formed of a suitable plastic material, as is known. Although a dispenser bottle is not shown in this embodiment, this system 1100 can be configured for use with threaded nasal sprayer dispenser bottles, such as shown in FIGS. 1-30, although the example embodiments are not so limited to use with nasal sprayer dispensers.

The cap 1110 is 3-sided to minimize rolling and avoid losing the cap 1110. Cap 1110 includes a pair of spaced legs 1111, with each leg 1111 having a lower rib 1115, an upper wing 1116, and a leg slot 1118 formed above the wing 1116 and terminating at a notch 1117. The dispensing tip 1120 includes shoulders 1121 which has slots 1123 formed there through. A user depresses the shoulders 1121 to actuate the sprayer pump unit within (not shown). The base 1130 includes interior threaded grooves (not shown), an aperture 1134 for receiving a nozzle of a sprayer pump unit (not shown) there through into the dispensing tip 1120 and an inner circumferential rib 1132 for engagement with the legs 1111 when in a locked condition. A spacing 1135 is provided when the cap is rotated to un-engage the legs 1111 from the rib 1132 and withdrawal the cap from the dispensing tip 1120.

Optionally, the base 1130 can have the configuration shown in FIG. 11. Specifically, the base can be configured with serrations (teeth) on its skirt, so as to form a mechanical bond with a dispenser bottle upon screwing the base down onto the threads of the dispenser bottle to seat the system 1100 on the bottle.

Figures 61, 62, 63:
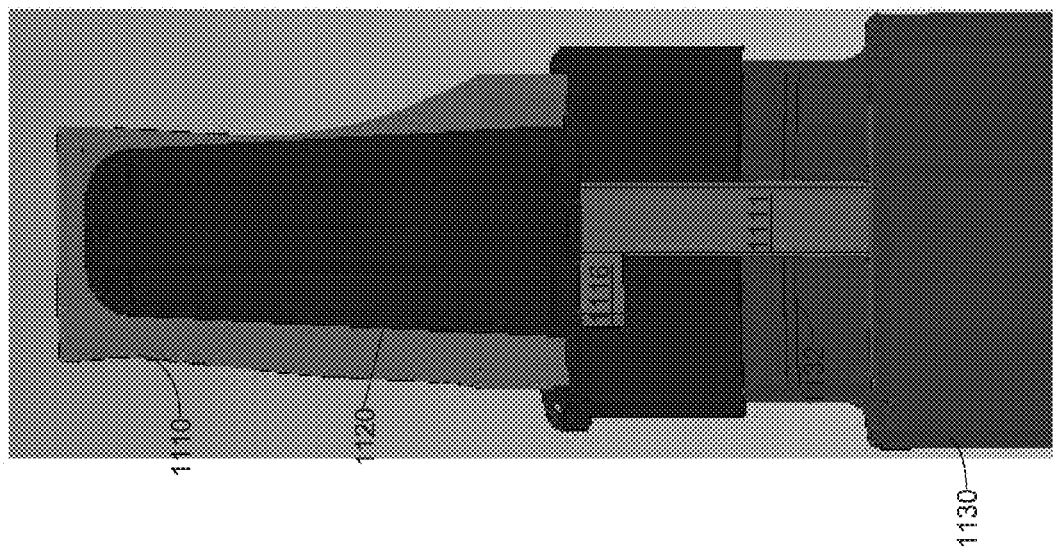
FIG. 61 is a close-up of a bottom underside view of a portion of the dispensing tip.
FIG. 62 is an enlarged side view of a portion of the upper leg of the cap.
FIG. 63 is a sectional view of the system taken in the yz plane.

FIG. 61 is a close-up of a bottom underside view of a portion of the dispensing tip, and FIG. 62 is an enlarged side view of a portion of the upper leg of the cap. These two figures illustrate the relationship between a tab 1127 on the underside of shoulders 1121 behind slot 1123, and a notch 1117 on the wing 1116 of leg 1111. As the leg 1111 is inserted into slot 1123 and rotated, leg 1111 rotation is terminated once the tab 1127 is captured by the notch 1117. There is a notch 1117 on each leg and a tab 1127 next to each slot on the underside of the dispensing tip 1120.

FIG. 63 is a sectional view of the system taken in the yz plane. As shown in FIG. 63, in the locked condition, the leg 1111 extends all the way down through the bottom of the dispensing tip 1120 to the base 1130. Specifically, lower rib 1115 catches the centrally formed inner rib 1132 on base 1130 to lock leg 1111 in place. Recall also that rotation of the cap 1110 to the locked position causes tab 1127 on the underside of slot 1123 to ride in leg slot 1118 as the leg 1111 rotates, with leg 1111 rotation terminating once the tab 1127 is captured in notch 1117. Accordingly, the shoulders 1121 cannot be depressed, and actuation is locked out.

FIG. 64 is a front view of a child-resistant closure system for a pump assembly according to another example embodiment, FIG. 65 is a side view of the assembly of FIG. 64, FIG. 66 is a perspective view of the assembly of FIG. 64 with a different pump cap, and FIG. 67 is an exploded view of selected components of the system of FIG. 64. Referring to FIGS. 64-67, the child-resistant closure (CRC) system 1200 includes a cap 1210, a pump head 1215 with spout 1216, a dispenser 1220 and a base 1230. Each of the cap 1210, pump head 1215, spout 1216, dispenser 1220 and base 1230 may be injection molded or extruded or otherwise formed of a suitable plastic material, as is known. The dispenser bottle is not shown, although it is a bottle that may hold a liquid having a viscosity higher than water, examples being a lotion, shampoo, sunscreen, baby oil and the like, although the CRC system 1200 and associated pump assembly are not so limited to handling liquids of these viscosities. Accordingly, there is included a tank 1240 which holds a portion of the liquid in the bottle. The tank 1240 is secured at its upper end by a bottle cap (not shown), as is known, which in turn is threadingly engaged within the interior of the lower portion of base 1230.

The cap 1210 includes a rim 1213 at its bottom and terminates in a pair of spaced legs 1211. The legs 1211 are designed to be inserted into slots 1223 in the top of dispenser 1220 to lock out actuation of the pump head 1215. The cap includes an inverse L-shaped aperture 1214 that has locked and unlocked positions for spout 1216.

Figure 69:
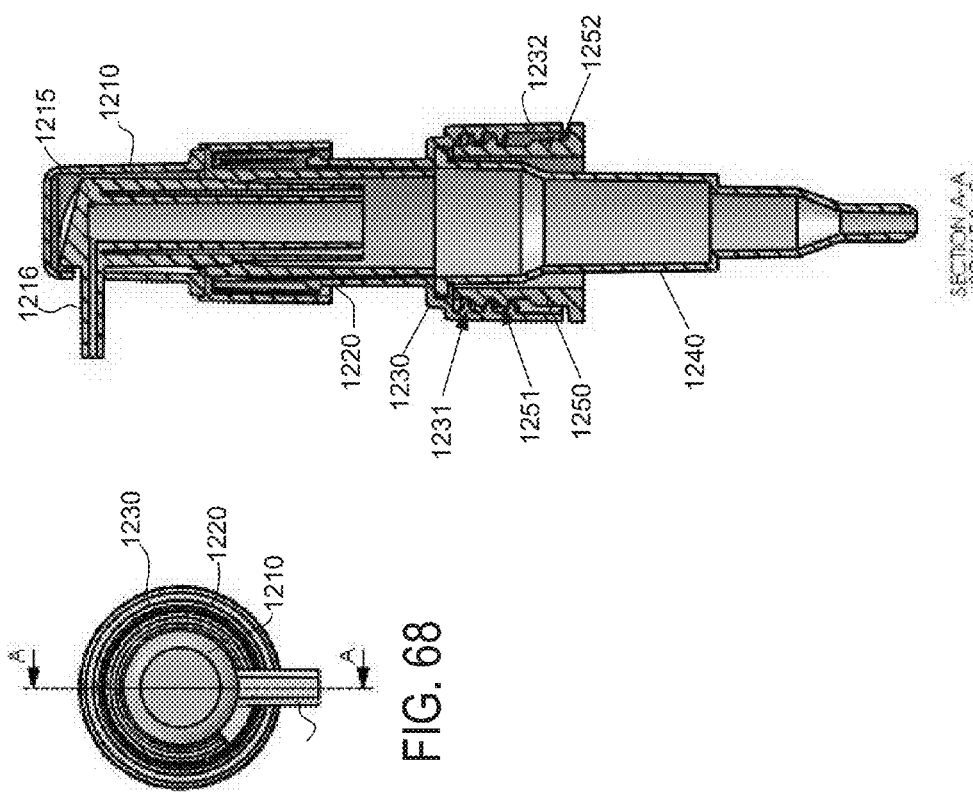
FIG. 69 is sectional view A-A taken from FIG. 68.
Figure 68:
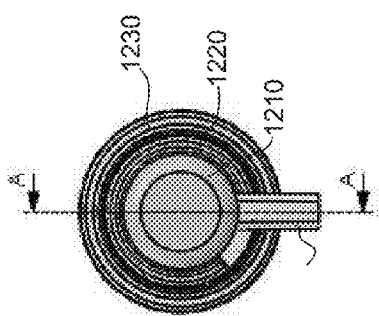
FIG. 68 is a top view of the assembly of FIG. 64.

FIG. 68 is a top view of the assembly of FIG. 64, and FIG. 69 is sectional view A-A taken from FIG. 68. FIG. 69 shows the engagement of the bottle cap 1250 to the tank 1240 and the engagement of the bottle cap 1250 and tank 1240 to the base 1230. Specifically, the base includes interior grooves 1231 which mate with exterior threads 1251 on cap 1250. Optionally, the base 1230 can have the configuration shown in FIG. 11. Specifically, the base 1230 can be configured with serrations (teeth) on its skirt (shown by arrow 1232), so as to form a mechanical bond with corresponding teeth or serrations (shown by arrow 1252) formed on the bottle cap skirt, upon screwing the base 1230 down onto the threads 1251 of the bottle cap 1250 to seat the system 1200 on the dispenser bottle.

Figure 70:
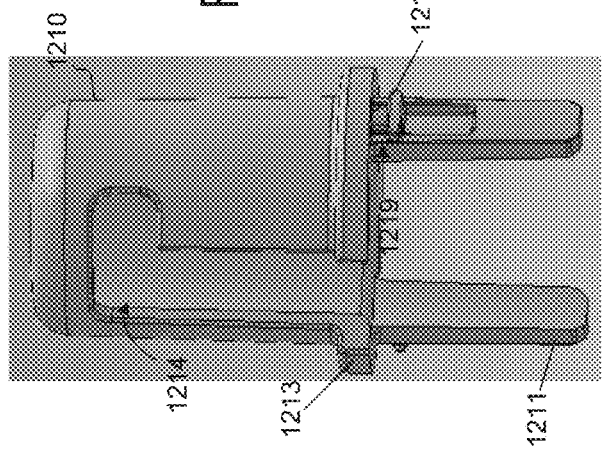
FIG. 70 is a perspective view of the pump cap of the system.
Figure 71:
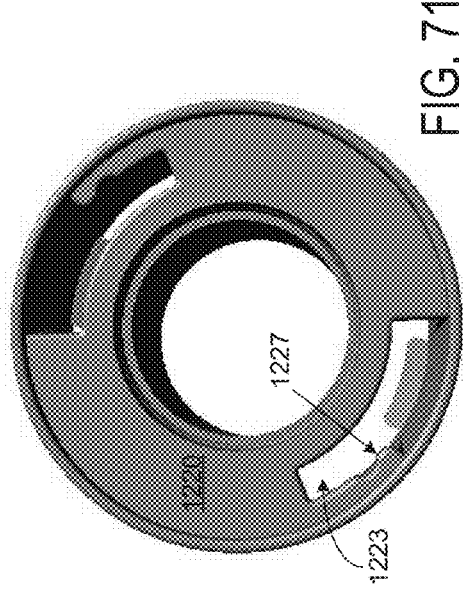
FIG. 71 is a top view of the dispenser according to the system.

FIG. 70 is a perspective view of the pump cap of the system, and FIG. 71 is a top view of the dispenser according to the system. The cap 1210 includes the aforementioned two legs 1211 which are tapered. Each leg includes an outer rib 1218 near its top, with an undercut 1219 sandwiched between the rib 1218 and the rim 1213 of the cap 1210. The dispenser 1220 includes a pair of facing slots 1223. Each slot 1223 includes a detent 1227 therein. The detents 1227 interface with the legs 1211 as the legs 1211 rotate in the slots 1223.

Figure 73:
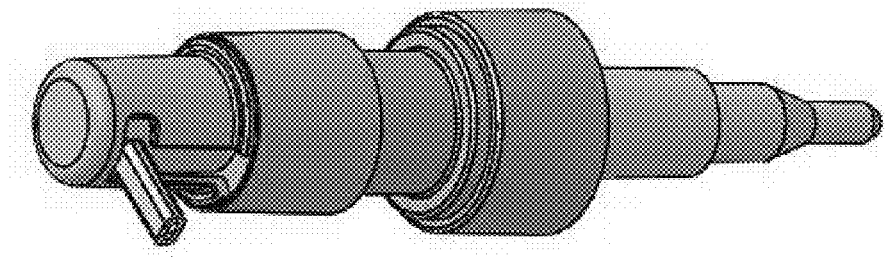
FIG. 73 is a perspective view of the assembly of FIG. 64 showing an unlocked condition.
Figure 72:
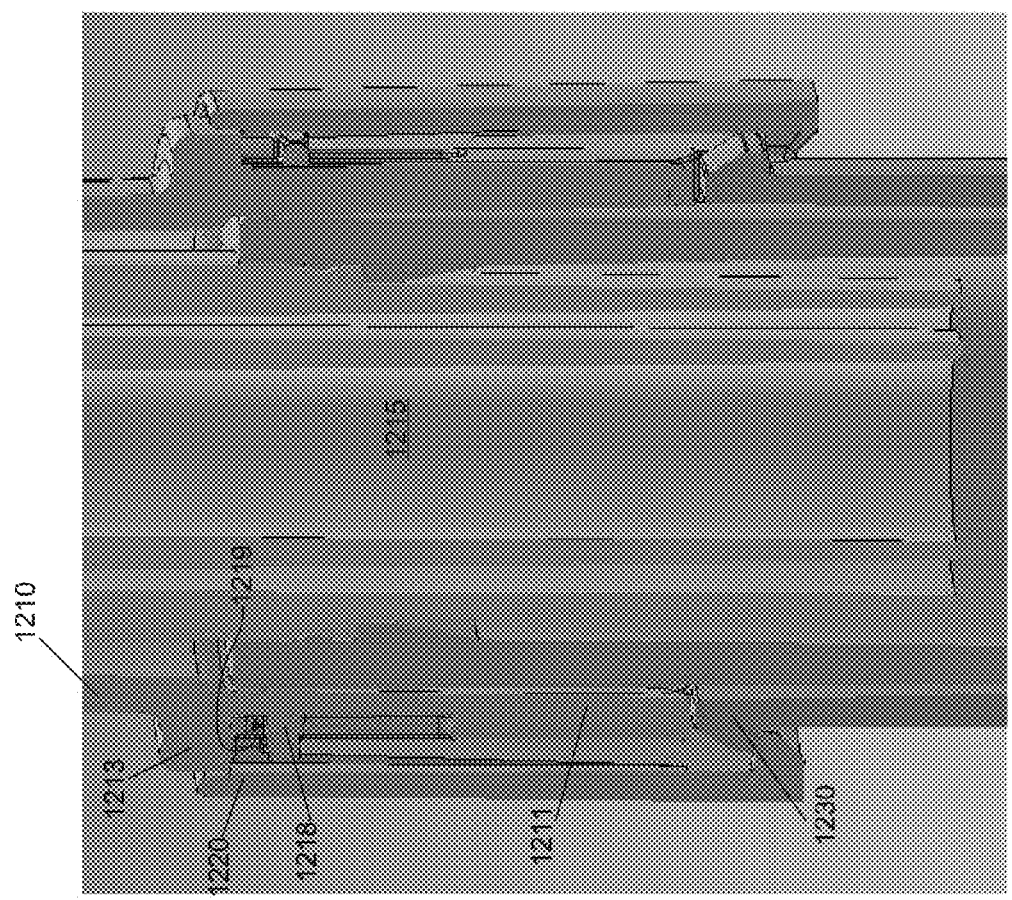
FIG. 72 is a sectional view taken in the xy plane of a portion of the system to show a locked condition thereof.

FIG. 72 is a sectional view taken in the xy plane of a portion of the system to show a locked condition thereof, and FIG. 73 is a perspective view of the assembly of FIG. 64 showing an unlocked condition. In operation, with the cap 1210 in place in the slots 1223, operation of the pump head 1215 is locked out. The cap 1210 is retained by the two legs 1211 which are tapered, with the horizontal undercut 1219 which engages with the underside of the dispenser 1220 while in slot 1223. When engaging, the cap 1210 is placed and turned in a clockwise motion, which engages the undercuts 1219 with the underside of the dispenser 1220. While turning, the legs 1211 of the cap 1210 will pass the two detents 1227 in slots 1223 and produce a tangible click, which indicates full engagement. As shown in FIG. 72, the legs 1210 extend to the top of the base 1230 and allow for the dispenser 1220 to be locked out while the cap 1210 is in place. Accordingly, the pump head 1215 cannot be actuated.

To release the cap 1210, the cap 1210 can be turned counter clockwise, as shown in FIG. 73, and then the cap 1210 is drawn up so the legs 1211 are removed out of the slots 1223 and off of the dispenser 1220. With the cap removed, the pump head 1215 is now free to dispense.

FIG. 74 is a front view of a child-resistant closure system for a pump assembly according to another example embodiment, FIG. 75 is an exploded view of selected components of the system of FIG. 74, and FIG. 76 is a perspective view of the pump cap of the system. Referring to FIGS. 74-76, the child-resistant closure (CRC) system 1300 includes a cap 1310, a pump head 1315 with spout 1316, a dispenser 1320 and a base 1330. Each of the cap 1310, pump head 1315, spout 1316, dispenser 1320 and base 1330 may be injection molded or extruded or otherwise formed of a suitable plastic material, as is known. The dispenser 1320 includes a pair of spaced buttons 1322 on opposite sides of a collar 1326 of the dispenser 1320 to allow cap 1310 removal and permit actuation of pump head 1315.

The dispenser bottle is not shown, although it is a bottle that may hold a liquid having a viscosity higher than water, examples being a lotion, shampoo, sunscreen, baby oil and the like, although the CRC system 1300 and associated pump assembly are not so limited to handling liquids of these viscosities. Accordingly, there is included a tank 1340 which holds a portion of the liquid in the bottle. The tank 1340 is secured at its upper end by a bottle cap (not shown), as is known, which in turn is threadingly engaged within the interior of the lower portion of base 1330.

The cap 1310 is 3-sided to minimize rolling and avoid losing the cap 1310. The cap 1310 includes a rim 1313 at its bottom and terminates in a pair of spaced legs 1311. The legs 1311 are designed to be inserted into slots 1323 in the top of dispenser 1320 to lock out actuation of the pump head 1315. The cap includes an inverse L-shaped aperture 1314 that has locked and unlocked positions for spout 1316. FIG. 74 shows the spout 1316 in the unlocked position within aperture 1314. Each leg 1311 has an outer rib 1318 at an upper portion thereof with an undercut sandwiched between the rib 1318 and the rim 1313 of cap 1310.

FIG. 77 is a top view of the dispenser according to the system, FIG. 78 is sectional view A-A taken from FIG. 77, and FIG. 79 is a portion of a sectional view of the dispenser and legs in the xz-plane from a bottom viewpoint with selected components removed to illustrate a locked condition. Additionally, FIG. 79A is a sectional view taken in the xy plane of a portion of the system to show a locked condition thereof. Referring to FIGS. 77 to 79, there is shown the engagement of the bottle cap 1350 to the tank 1340 and the engagement of the bottle cap 1350 and tank 1340 to the base 1330. Specifically, the base includes interior grooves 1331 which mate with exterior threads 1351 on cap 1350. Optionally, the base 1330 can have the configuration shown in FIG. 11. Specifically, the base 1330 can be configured with serrations (teeth) on its skirt (shown by arrow 1332), so as to form a mechanical bond with corresponding teeth or serrations (shown by arrow 1352) formed on the bottle cap skirt, upon screwing the base 1330 down onto the threads 1351 of the bottle cap 1350 to seat the system 1300 on the dispenser bottle.

In operation, with the cap 1310 in place and the legs 1311 secured in the slots 1323, actuation of the pump head 1315 is locked out. Specifically, the cap 1310 is retained by the two legs 1311 which are tapered, with horizontal undercuts that engage with tabs 1327 that extend from a backside of a relief portions 1324 on the buttons 1322 on the dispenser 1320, as shown in FIG. 79. When engaging, the cap 1310 is placed and turned in a clockwise motion, which will press the legs 1311 against the tabs 1327 extending from the underside of the relief portions 1324 of the buttons 1322, as shown in FIG. 79. This in turn forces the tabs 1327 to deflect outwards until the undercuts on the cap 1310 pass. Once clear, the tabs 1327 snap into position behind the undercuts on the legs 1311 and lock the cap 1310 in place. As best shown in FIG. 78, the legs 1311 extend to the top of the base 1330 and allow for the dispenser 1320 to be locked out while the cap 1310 is in place.

To release the cap 1310, the buttons 1322 on the cap 1310 must be simultaneously pressed in a horizontal inward motion. This causes the ramps 1327 on reliefs 1324 to cant outward by way of the cam action of hinges 1325, which in turn causes the legs 1311 to deflect outwards. The user then rotates the cap 1310 30 degrees (into the wider part of slot 1323) after having depressed both buttons 1322 to release the cap 1310 from the dispenser 1320. This also places spout 1316 in the unlocked position in aperture 1314, as shown in FIG. 74. The cap 1310 can then be removed, so that actuation of pump head 1315 is now possible.

FIG. 80 is a perspective view of a child-resistant closure system for a pump assembly according to another example embodiment, and FIG. 81 is an exploded view of selected components of the system of FIG. 80. Referring to FIGS. 80 and 81, the child-resistant closure (CRC) system 1400 includes a cap 1410, a pump head 1415 with spout 1416 extending through aperture 1414, a dispenser 1420 and a base 1430. Each of the cap 1410, pump head 1415, spout 1416, dispenser 1420 and base 1430 may be injection molded or extruded or otherwise formed of a suitable plastic material, as is known. The cap 1410 includes a pair of spaced buttons 1412 on opposite sides thereof to allow cap 1410 removal and permit actuation of pump head 1415.

The dispenser bottle is not shown, although it is a bottle that may hold a liquid having a viscosity higher than water, examples being a lotion, shampoo, sunscreen, baby oil and the like, although the CRC system 1400 and associated pump assembly are not so limited to handling liquids of these viscosities. Accordingly, there is included a tank 1440 which holds a portion of the liquid in the bottle. The tank 1440 is secured at its upper end by a bottle cap (not shown), as is known, which in turn is threadingly engaged within the interior of the lower portion of base 1430.

FIG. 82 is a front view of the pump cap of the system, and FIG. 83 is a rear perspective view of the cap of FIG. 82. Referring to FIGS. 82 and 83, the cap 1410 is 3-sided to minimize rolling and avoid losing the cap 1410. The cap 1410 includes a slit or relief 1417 on one side of each button 1412 to provide flexibility for the button 1412. The rear of the cap has a hollowed out opening 1409 so that it can be easily removed from the pump head 1415 once in the unlocked condition. The cap 1410 includes a rim 1413 at its bottom and terminates in a pair of spaced legs 1411. The legs 1411 are designed to be inserted into slots 1423 in the top of dispenser 1420 (see FIG. 81) to lock out actuation of the pump head 1415. Each leg 1411 is tapered and has an outer rib 1418 at an upper portion thereof with an undercut sandwiched between the rib 1418 and the rim 1414 of cap 1410.

FIG. 84 is a top view of the system of FIG. 80, and FIG. 85 is sectional view A-A taken from FIG. 85. Referring to FIGS. 84 and 85, there is shown the engagement of the bottle cap 1450 to the tank 1440 and the engagement of the bottle cap 1450 and tank 1440 to the base 1430. Specifically, the base 1430 includes interior grooves 1431 which mate with exterior threads 1451 on cap 1450. Optionally, the base 1430 can have the configuration shown in FIG. 11. Specifically, the base 1430 can be configured with serrations (teeth) on its skirt (shown by arrow 1432), so as to form a mechanical bond with corresponding teeth or serrations (shown by arrow 1452) formed on the bottle cap skirt (similar to as shown on the bottle skirt of FIGS. 12 and 13), upon screwing the base 1430 down onto the threads 1451 of the bottle cap 1450 to seat the system 1400 on the dispenser bottle.

FIG. 86 is a sectional view taken in the xy plane of a portion of the system to show a locked condition thereof. FIG. 86 is provided to help describe the locked and unlocked conditions for cap 1410. With the cap 1410 in place and the legs 1411 secured in the slots 1423, actuation of the pump head 1415 is locked out. Specifically, the cap 1410 is retained by the two legs 1411 that are tapered, with undercuts 1419 that engage with the underside of the slots 1423 on the dispenser 1420. When engaging, the legs 1411 will deflect inwards until the undercuts 1419 pass the slots on the dispenser 1420, where the legs 1411 will snap back to vertical and engage, with a portion of the dispenser 1420 captured in the undercuts 1419 between the ribs 1418 and rim 1413 off the legs 1411. The legs 1411 extend to the top of the base 1430 and allow for the dispenser 1420 to be locked out while the cap 1410 is in place. Accordingly, operation of the pump head 1415 is locked out.

To release the cap 1410 into an unlocked condition, the buttons 1412 on the cap 1410 must be pressed simultaneously, causing the legs 1411 to once again deflect inwards and the cap 1410 can be drawn up and off of the dispenser 1420. With the cap 1410 removed off of spout 1416, the pump head 1415 is now free to dispense.

FIG. 87 is a front view of a child-resistant closure system for a pump sprayer according to another example embodiment, FIG. 88 is a perspective view of a cap according to the system of FIG. 87, and FIG. 89 is a bottom perspective view of a dispensing tip according to the system of FIG. 87. System 1500 is identical to system 200 previously described above, with the exception that only one button is present on dispensing tip 1520 and only one leg 1511 is included on cap 1510. Otherwise, all other functionality of the system 1500 follows that of FIGS. 7-16 which describe system 200. Accordingly, a refresher on the operation and mechanical bonds formed when the cap 1510 is in place on the dispensing tip 1520 is hereafter described.

FIG. 90 is a portion of a sectional view taken of the system in the xy-plane to show a locked condition. In addition to the mechanical bond formed between the serrated teeth (not shown) on the lower skirt of base 1530, which engages with teeth on dispenser bottle skirt 1540 (referring back to the anti-back off feature first described in FIGS. 11-13, which is applicable both the system 200 and here), FIG. 90 shows where a portion of the dispensing tip 1520 on the underside of slots 1523 is captured between the rim 1513 of leg 1511 and the rib 1515. The leg 1511 also extends all the way down to base 1530, locking out actuation.

In operation, once the cap 1510 is placed on the dispensing tip 1520, the leg 1511 travels through the slot 1523 and rides over the ramp 1527 to lock into place. In this locked condition, a portion of the dispensing tip 220 is retained between the rim 1513 of cap 1510 and the rib 1515, as best seen in FIG. 90. The leg 1511 extends all the way down to the base 1530, locking out movement of the shoulders 1521 and hence sprayer pump unit 1550.

To unlock for operation, the user depresses the button 1522 inward. This causes the ramp 1527 to cant outward by way of the cam action of hinge 1525. This allows leg 1511 free travel. The user then rotates the cap 1510 and draws it up off of the dispensing tip 1520. With the cap 1510 removed, actuation is now possible via shoulders 1521.

FIG. 91 is a perspective view of a child-resistant closure system for a pump sprayer according to another example embodiment, and FIG. 92 is an exploded view of the system of FIG. 91. System 1600 is identical to system 600 previously described above, with the exception that the retainer collar 630 has been replaced with a modified crimp seal 1645, and the top of the dispenser bottle at the ferrule portion 641 has been modified to add a lip 1643 for the crimp seal 1645. Otherwise, all other functionality of the system 1600 follows that of FIGS. 31-36 which describe system 1600. Accordingly, a refresher on the operation and mechanical bonds formed when the cap 1610 is in placed on the dispensing tip 1620 is hereafter described.

FIG. 93 is a portion of a sectional view taken of the system in the xy-plane to show a locked condition. Initially, the mechanical bond formed with the crimp seal 1645 is described. Referring to FIG. 93, and noting that any ferrule body embodiment utilizing a retainer collar may be replaced with the following, the inventors modified the ferrule portion 1641 of the dispenser bottle 1640 to add a lip 1643. A metallic or synthetic crimp seal 1645 was then added, crimped at a substantial pressure, so as to seat at the underside of the rim 1643, to form a mechanical bond with the rim 1643 as it engages an inner wall surface of dispenser tip 1620.

In operation, with the cap 1610 inserted through the slots 1623, the legs 1611 contacting base 1630, operation of the shoulders 1621 is locked out; actuation of sprayer pump unit 1650 is not possible. Specifically, the cap 1610 is retained by the two legs 1611, with undercuts 16116 that engage with the underside of the slots 1623 on the shoulders 1621 of the dispensing tip 1620, and the two tabs 1614 that extend from the levers 1612 on the cap 1610. When engaging, the legs 1611 will pass the slots 1623 and engage with the dispensing tip 1620 once turned clockwise. At the end of the turning motion, the tabs 1614 deflect downward and engage with the shoulder 1621 portion at slot 1623 to lock out the cap 1610 and keep it from disengagement. As noted, the legs 1611 extend to the top of the base 1630 and allow for the sprayer pump unit 1650 (by way of shoulders 1621) to be locked out while the cap 1610 is locked in place.

To release the cap 1610, the levers 1612 must be pressed inward simultaneously, causing the tabs 1614 to deflect upwards. The cap 1611 is then turned in a counter-clockwise motion, drawn up through wider portion of slot 1623, and off of the dispensing tip 1620. With cap 1610 removed, downward movement of the shoulders 1621 to actuate the sprayer pump unit 1650 is possible.

FIG. 94 is a front view of a child-resistant closure system for a pump assembly according to another example embodiment, FIG. 95 is an exploded view of selected components of the system of FIG. 94, and FIG. 96 is a top view of the dispenser according to the system. System 1700 is identical to system 1300 previously described above, with the exception that the spouted pump unit has been replaced with a spray pump unit. Otherwise, all other functionality of the system 1700 follows that of FIGS. 74-79 which describe system 1300. Accordingly, a refresher on the operation and mechanical bonds formed when the cap 1710 is in placed on the dispenser 1720 is hereafter described.

FIG. 97 is sectional view A-A taken from FIG. 96. Reference should be made to FIG. 79 as well for the following discussion, which shows specifics of the dispenser 1320/1720 in cross section with the legs (same construction). In operation, with the cap 1710 in place and the legs 1711 secured in the slots 1723, actuation of the pump head 1715 is locked out. Specifically, the cap 1710 is retained by the two legs 1711 which are tapered, with horizontal undercuts that engage with tabs 1327 (1727) that extend from a backside of a relief portions 1324 (1724) on the buttons 1722 on the dispenser 1720 (see related references in FIG. 79). When engaging, the cap 1710 is placed and turned in a clockwise motion, which will press the legs 1711 against the tabs 1327 (1727) extending from the underside of the relief portions 1324 (1724) of the buttons 1722 (see FIG. 79 for related element numbers). This in turn forces the tabs 1327 (1727) to deflect outwards until the undercuts on the cap 1710 pass. Once clear, the tabs 1327 (1727) snap into position behind the undercuts on the legs 1711 and lock the cap 1710 in place. As best shown in FIG. 97, the legs 1711 extend to the top of the base 1730 and allow for the dispenser 1720 to be locked out while the cap 1710 is in place.

To release the cap 1710, the buttons 1722 on the cap 1710 must be simultaneously pressed in a horizontal inward motion. This causes the tabs 1327 (1727) to cant outward by way of the cam action of hinges 1325 (1725), which in turn causes the legs 1711 to deflect outwards. The user then rotates the cap 1710 30 degrees (into the wider part of slot 1723) after having depressed both buttons 1722 to release the cap 1710 from the dispenser 1720. The cap 1710 can then be removed, so that actuation of pump head 1715 is now possible.

The example embodiments being thus described, it will be obvious that the same may be varied in many ways. Such variations are not to be regarded as departure from the example embodiments, and all such modifications as would be obvious to one skilled in the art are intended to be included in the following claims.

We claim:

1. A child-resistant closure system for a pump sprayer, comprising:

a cap having a rim at its lower end and including at least one leg extending downward from the rim, the leg including an outwardly projecting vertical protrusion and an outwardly extending horizontal rib, with an undercut provided between the rib and the rim of the cap;

a dispensing tip configured to receive the cap thereon, a lower end of the dispensing tip including a horizontal circumferential portion and a pair of finger-depressing shoulders in opposite relation to one another extending horizontally outward from the horizontal circumferential portion, at least one slot defined in the horizontal circumferential portion of the dispensing tip, the slot comprising a wider insertion/removal portion for inserting or removing the leg of the cap therethrough and a narrower locking portion for engaging the leg for locking the cap to the dispensing tip, the dispensing tip having a cylindrical collar provided beneath the shoulders, the collar including at least one button on a vertical facing of the collar, the button comprising a vertical protrusion on an internal side that engages with the vertical protrusion of the leg to prevent rotation of the cap relative to the dispensing tip from a locked condition to an unlocked condition, the button configured to be actuated to enable rotation of the cap relative to the dispensing tip from the locked condition to the unlocked condition so as to enable removal of the cap off of the dispensing tip; and a base secured to the collar of the dispensing tip and secured to a dispenser bottle which contains fluid, the dispenser bottle including a sprayer pump unit which partly extends into an interior of the dispenser bottle and which is actuated by depressing the shoulders on the dispensing tip to spray the fluid within the dispenser bottle;

wherein the cap is selectively received by the dispensing tip by inserting the leg of the cap into the wider insertion/removal portion of the slot until the leg contacts the top of the base;

wherein the cap is selectively secured to the dispensing tip so as to prevent actuation of the sprayer pump by rotating the cap such that the leg moves from the wider insertion/removal portion of the slot to the narrower locking portion of the slot, such that at least a portion of an edge of the narrower locking portion of the slot engages the undercut provided between the rib of the leg and the rim of the cap, and such that the vertical protrusion of the leg engages with the vertical protrusion on the internal side of a corresponding button;

wherein, with the cap in place on the dispensing tip, the leg extends downward through the slot to contact the top of the base so as to allow for the sprayer pump unit to be locked out from operation; and wherein, to remove the cap so as to permit actuation of the sprayer pump unit via the shoulders, the button on the collar is pressed to disengage the vertical protrusion of the leg and the vertical protrusion on the internal side of the button so that the cap may be rotated from the locked condition to the unlocked condition so as to enable removal of cap off of the dispensing tip.

2. The child-resistant closure system of claim 1, wherein:
the at least one leg comprises a pair of legs, each leg in opposite relation to one another and extending downward from the rim, each leg including an outwardly projecting vertical protrusion and an outwardly extending horizontal rib, with an undercut provided between each rib and the rim of the cap;

wherein the at least one slot comprises a pair of spaced apart slots defined in the horizontal circumferential portion of the dispensing tip, each slot comprising a wider insertion/removal portion for inserting or removing a corresponding leg of the cap therethrough and a narrower locking portion for engaging the corresponding leg for locking the cap to the dispensing tip;

wherein the at least one button comprises a pair of buttons in opposite relation to one another on the vertical facing of the collar, each button comprising a vertical protrusion on an internal side that engages with the vertical protrusion of a corresponding one of the legs to prevent rotation of the cap relative to the dispensing tip from a locked condition to an unlocked condition, the buttons configured to be simultaneously actuated to enable rotation of the cap relative to the dispensing tip from the locked condition to the unlocked condition so as to enable removal of the cap off of the dispensing tip;

wherein the cap is selectively received by the dispensing tip by inserting each leg of the cap into the wider insertion/removal portion of a corresponding slot until the legs contact the top of the base;

wherein the cap is selectively secured to the dispensing dip so as to prevent actuation of the sprayer pump by rotating the cap such that each leg moves from the wider insertion/removal portion of the corresponding slot to the narrower locking portion of the corresponding slot, such that at least a portion of an edge of the narrower locking portion of the corresponding slot engages the corresponding undercut provided between the rib of the corresponding leg and the rim of the cap and such that the vertical protrusion of each leg engages with the vertical protrusion on the internal side of a corresponding button;

wherein, with the cap in place on the dispensing tip, the legs extend downward through the slots to contact the top of the base so as to allow for the sprayer pump unit to be locked out from operation; and wherein, to remove the cap so as to permit actuation of the sprayer pump unit via the shoulders, the buttons on the collar are pressed simultaneously to disengage the vertical protrusion of each leg and the vertical protrusion on the internal side of the corresponding button so that the cap may be rotated from the locked condition to the unlocked condition so as to enable removal of cap off of the dispensing tip.

3. The child-resistant closure system of claim 1, wherein each button comprises a first end and second end separated by a vertical hinge, such that depressing the first end inward causes the second end to pivot outward;

wherein the vertical protrusion is on an internal side of the second end;

wherein the vertical protrusion of each button engages with the vertical protrusion of a corresponding one of the legs when the respective first end is not depressed, thereby preventing rotation of the cap relative to the dispensing tip from the locked condition to the unlocked condition; and wherein the vertical protrusion of each button disengages from the corresponding one of the legs when the respective first end is depressed, thereby allowing rotation of the cap relative to the dispensing tip from the locked condition to the unlocked condition.

* * * * *